(12) United States Patent
Auner et al.

(10) Patent No.: US 11,192,104 B2
(45) Date of Patent: Dec. 7, 2021

(54) RAPID ASSESSMENT DEVICE FOR RADIATION EXPOSURE

(71) Applicant: VISCA, LLC, Troy, MI (US)

(72) Inventors: Gregory W. Auner, Livonia, MI (US); Michelle A. Brusatori, Sterling Heights, MI (US); Changhe Huang, Novi, MI (US)

(73) Assignee: Visca, LLC, Troy, MI (US)

( * ) Notice: Subject to any disclaimer, the term of this patent is extended or adjusted under 35 U.S.C. 154(b) by 0 days.

(21) Appl. No.: 16/761,746

(22) PCT Filed: Nov. 9, 2018

(86) PCT No.: PCT/US2018/060112
§ 371 (c)(1),
(2) Date: May 5, 2020

(87) PCT Pub. No.: WO2019/118109
PCT Pub. Date: Jun. 20, 2019

(65) Prior Publication Data
US 2020/0261909 A1    Aug. 20, 2020

Related U.S. Application Data

(60) Provisional application No. 62/584,199, filed on Nov. 10, 2017, provisional application No. 62/584,204, (Continued)

(51) Int. Cl.
*B01L 3/00* (2006.01)
*B01L 7/00* (2006.01)
*B01L 99/00* (2010.01)

(52) U.S. Cl.
CPC ... *B01L 3/502715* (2013.01); *B01L 3/502761* (2013.01); *B01L 3/50273* (2013.01);
(Continued)

(58) Field of Classification Search
CPC .............. C12Q 1/686; C12Q 2521/107; C12Q 2565/629; B01L 2200/10;
(Continued)

(56) References Cited

U.S. PATENT DOCUMENTS

2006/0017533 A1\* 1/2006 Jahnes ............... H01H 59/0009
                                                          335/78
2007/0241068 A1 10/2007 Pamula et al.
(Continued)

OTHER PUBLICATIONS

International Search Report and Written Opinion for PCT/US2018/060112 dated Aug. 27, 2019.
(Continued)

*Primary Examiner* — Gautam Prakash
*Assistant Examiner* — Lydia Edwards
(74) *Attorney, Agent, or Firm* — Visca, LLC

(57) ABSTRACT

A cartridge includes a substrate including a polymerase chain reaction (PCR) zone. The PCR zone includes a first heating region, a second heating region spaced away from the first heating region and a detection region. A microchannel is formed in the substrate. The microchannel receives a fluid flowing therethrough, the microchannel passing through the first heating region and second heating region to thermally cycle the fluid. The microchannel passes through the detection region after the fluid has been thermally cycled.

11 Claims, 35 Drawing Sheets

Related U.S. Application Data filed on Nov. 10, 2017, provisional application No. 62/584,208, filed on Nov. 10, 2017.

(52) U.S. Cl.
CPC .............. *B01L 7/52* (2013.01); *B01L 2200/10* (2013.01); *B01L 2300/0681* (2013.01); *B01L 2300/0816* (2013.01); *B01L 2300/0867* (2013.01); *B01L 2300/0883* (2013.01); *B01L 2400/0487* (2013.01)

(58) Field of Classification Search
CPC ....... B01L 2300/0883; B01L 2300/123; B01L 2400/0487; B01L 2400/086; B01L 3/00; B01L 3/502715; B01L 3/50273; B01L 3/502761; B01L 7/52; B01L 7/525; B01L 2300/0681; B01L 2300/0816; B01L 2300/0867; B32B 15/04; B32B 2307/412; B32B 2307/42; B32B 2457/20; B32B 3/30; C08J 5/18; G02B 1/118; G02B 1/18; G02B 5/30; G02B 5/3058

See application file for complete search history.

(56) References Cited

U.S. PATENT DOCUMENTS

| | | |
|---|---|---|
| 2010/0173394 A1 | 7/2010 | Colston, Jr. et al. |
| 2012/0178091 A1 | 7/2012 | Glezer et al. |
| 2012/0220494 A1 | 8/2012 | Samuels et al. |
| 2016/0199835 A1 | 7/2016 | Tachibana et al. |
| 2016/0289669 A1 | 10/2016 | Fan et al. |

OTHER PUBLICATIONS

Communication and Supplementary Partial European Search Report from EPO dated Jul. 1, 2021 regarding Application No. 18887794.8 (11 pages).

* cited by examiner

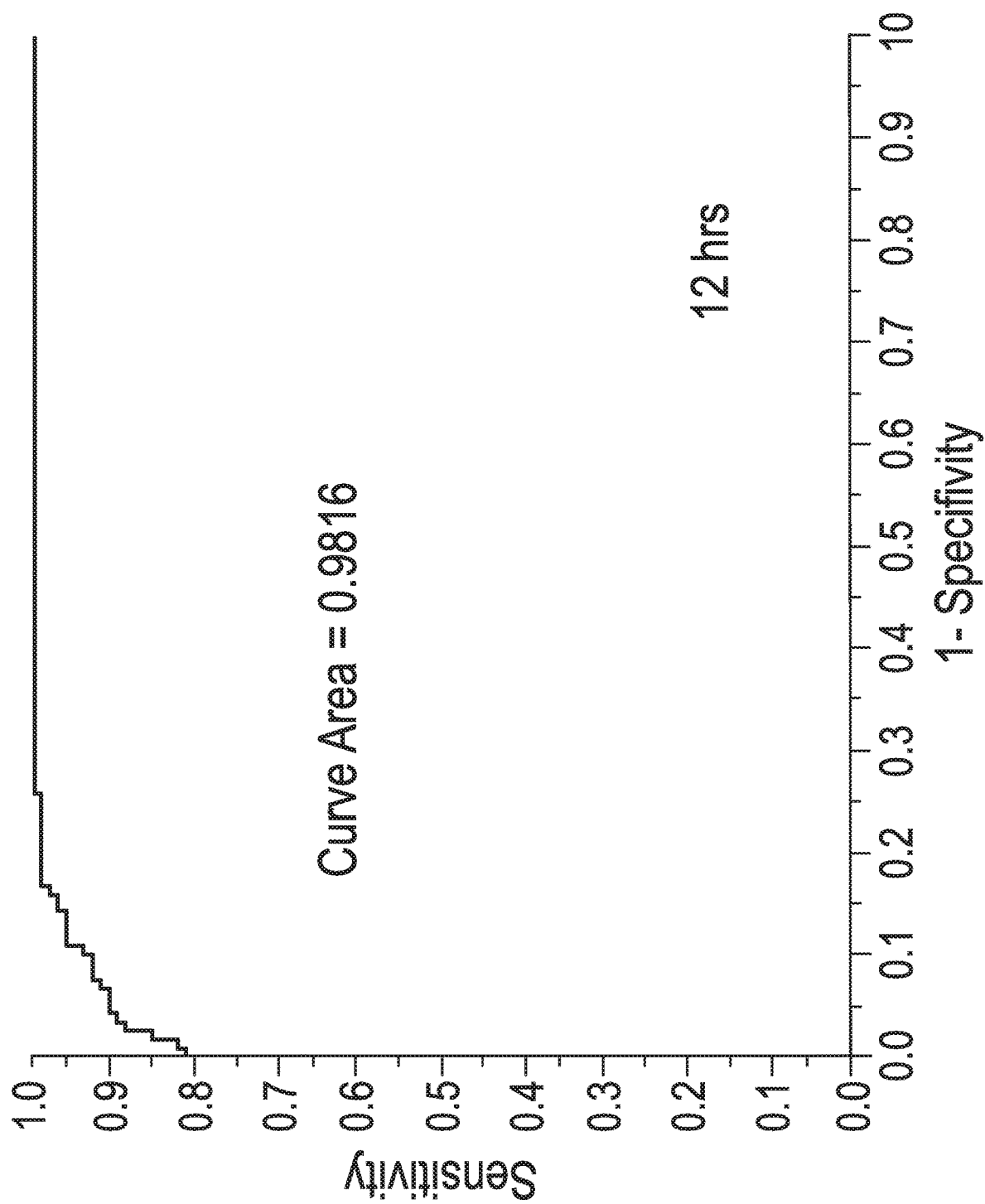

RAPID ASSESSMENT DEVICE FOR RADIATION EXPOSURE

CROSS-REFERENCE TO RELATED APPLICATIONS

This application claims priority to U.S. Provisional Application No. 62/584,199, filed on Nov. 10, 2017, and U.S. Provisional Application No. 62/584,204, filed on Nov. 10, 2017, and U.S. Provisional Application No. 62/584,208, filed on Nov. 10, 2017, which applications are hereby incorporated herein by reference in their entireties.

TECHNICAL FIELD

The present disclosure relates generally to a method and apparatus analyze components in a sample and in particular to determining an individual's level of exposure to radiation.

BACKGROUND

The ability to determine an individual's level of exposure to ionizing radiation (bio-dosimetry) due to a nuclear event is critical in the performing of triaging and determining the appropriate medical treatment of the exposed individuals. The following is a review of the current art for bio-dosimetry.

Molecular responses to ionizing radiation exposure fall in three broad categories according to the type of biomolecule chosen for analysis. These responses involve DNA, RNA, and protein.

Of these three, DNA responses occur first in the cell, i.e. DNA damage by radiation occurs instantly upon exposure. However, repair of the damage can take hours or even days to weeks, depending on the cell type and the nature of the damage. DNA damage occurs in several broad categories, including chromosomal breaks and rearrangements that are visible through the microscope, and point mutations including small (submicroscopic) deletions/insertions/rearrangements. Detection of chromosomal events is slow because the steps needed for their identification typically require cell culture followed by time-consuming analysis involving trained observers. The turn-around time is typically several days. Some chromosomal changes can be observed in cells that have not been cultured to metaphase, but these approaches require hybridization technologies followed by manual scoring involving trained observers.

Another type of cytogenetic response, that does not require cell culture, is the evaluation of micronuclei in erythrocytes. Micronuclei are formed by chromosomal fragments and by disruption of the mitotic spindle apparatus. Micronuclei are rare events and, in humans, erythrocytes bearing micronuclei are very efficiently filtered out by the spleen. In individuals who have had their spleen removed, micronucleated erythrocytes are not filtered out, and because the micronuclei are readily visible they can be efficiently counted by manual and by flow cytometric means. However, only about one adult per 1000 has been splenectomized, effectively negating this assay from broad-based population monitoring.

Another flow-cytometry-based approach might involve the analysis of rearranged chromosomes, e.g. dicentrics and/or translocations. In this approach, chromosomes that have undergone radiation-induced rearrangements would be detected and enumerated. Rearranged chromosomes would appear to be bi-colored because they would have been hybridized with whole chromosome paints in a manner that is analogous to in situ hybridization. However, for such flow-based analyses the chromosomes would need to remain in solution, meaning that hybridizations would also have to occur in solution. These chemistries have not been widely adapted due to technical difficulties related to the separation of unbound probe from the chromosomes.

Another approach to biological dosimetry involves protein analyses. Of the three biological response systems (DNA, RNA, protein), protein is the least well-characterized. There are several reasons why proteins may not be the subject of much research effort. First, the number of proteins is very large, perhaps an order of magnitude greater than the number of genes due to alternative splicing of mRNA and post-translational modification such as phosphorylation. Second, proteins often occur in complexes, sometimes making it difficult to enumerate quantities of specific peptide sequences. Third, proteins are all-too-readily denatured, which can interfere with common analysis methods such as enzyme-linked immunosorbent assay (ELISA). Finally, efficient quantitative analysis of proteins requires the use of monoclonal antibodies, which are not available for every protein, not to mention the vast array of protein variants that result from alternative splicing of mRNA and post-translational modification. Numerous changes to protein occur following irradiation. Unfortunately, the analytical techniques available for protein analysis lag substantially behind those for nucleic acid. To date, there are no systems using proteins that offer hope of performing meaningful biological dosimetry.

The third category of biological response to radiation is RNA. Specific RNA sequences are known to respond to ionizing radiation.

BRIEF DESCRIPTION OF THE DRAWINGS

FIG. 20A-20C illustrate example comparisons of modeling results with ex vivo human data respectively for 12 hours, 24 hours and 48 hours post exposure.

DETAILED DESCRIPTION

Figure 1:
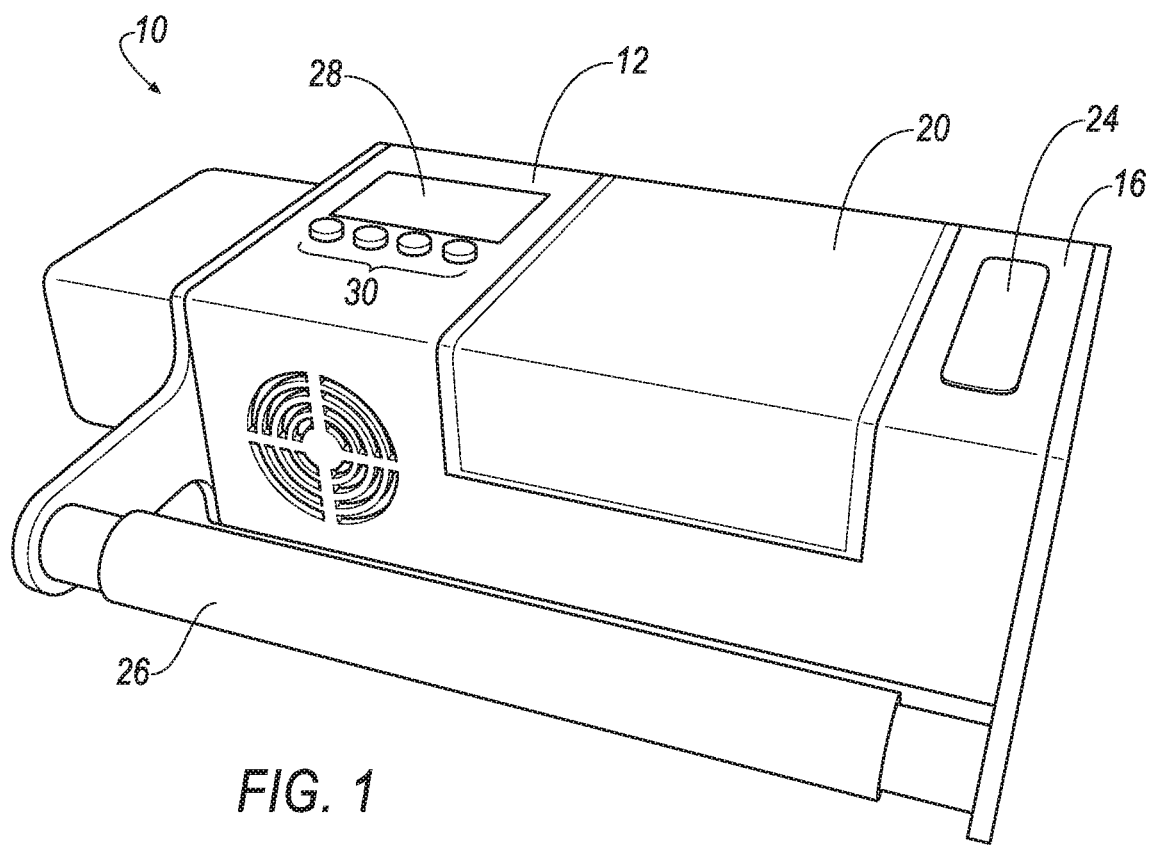
FIG. 1 is a perspective view of an example bio-dosimetry device.

RNA levels can be quantified quickly, easily, and inexpensively. Cell culture is not required, and every tissue contains RNA, so the analyses are not limited to a particular cell type. Significantly, RNA is readily reverse-transcribed into cDNA which can be amplified via the polymerase chain reaction (PCR) and quantified by real-time PCR. This means that very small amounts of tissue can be analyzed rapidly, efficiently, and quantitatively. Furthermore, RNA analyses take advantage of the very rapid response to ionizing radiation. Further, specific sequences of RNA undergo increased expression within an hour of exposure, while other genes continue to have elevated expression up to 24 hours, providing a flexible range of options for performing bio-dosimetry.

A portable bio-dosimetry system that can perform rapid and reliable testing of radiation exposure is needed. Disclosed is a handheld field deployable real-time quantitative polymerase chain reaction (qPCR) based system that can assess exposure of individuals to ionizing radiation based on the levels of specific mRNA sequences present in the leukocytes from a drop of blood. The drop of blood may be obtained, for example, by a finger stick in a field or triage setting following a nuclear event. The system can predict whether an individual has received a dose of ionizing radiation greater than or less than a predetermined threshold value to allow field medical personnel to identify individuals in urgent need of medical treatment and to determine exposure levels to aid in medical treatment.

The portable-dosimetry system includes sub-systems for receiving a blood sample from a person, lysing (breaking up of) blood cells from the blood sample into component parts including mRNA, binding the mRNA in a binding region for further processing while discarding waste from the lysing process, converting the bound mRNA to complimentary cDNA and performing quantitative polymerase chain reaction (qPCR) on the complimentary cDNA. The results of the qPCR analysis can provide an indication of exposure to radiation of the person.

FIGS. 1-4 illustrate an example bio-dosimetry system 10. The bio-dosimetry system 10 includes a bio-dosimetry device 12 and a cartridge 14 for processing a blood sample to determine the level of exposure to radiation of a respective person. As described in detail below, the bio-dosimetry device 12 may be a reusable, portable device that may be configured to receive one disposable cartridge 14 at a time, each cartridge 14 processing a blood sample of a respective person. The cartridge 14 is intended to be a single-use cartridge, used to measure a single sample. The bio-dosimetry device 12, performs a number of functions on the sample, including pumping, lysing, binding, conversion and PCR analysis. Based on these operations, the bio-dosimetry device 12 can determine a level of exposure to radiation of the blood sample.

As an example, the bio-dosimetry system 10, along with the various sub-systems and related processes, will be described in relation to analyzing a blood sample for exposure to radiation. It is envisioned within the context of this disclosure that the bio-dosimetry system 10 and/or some of the sub-systems, can be used for other applications such as analyzing cancer cells, types of cells (phenotypes) such as with use of flow cytometry, RNA viruses, types of bacteria, etc.

Figure 2:
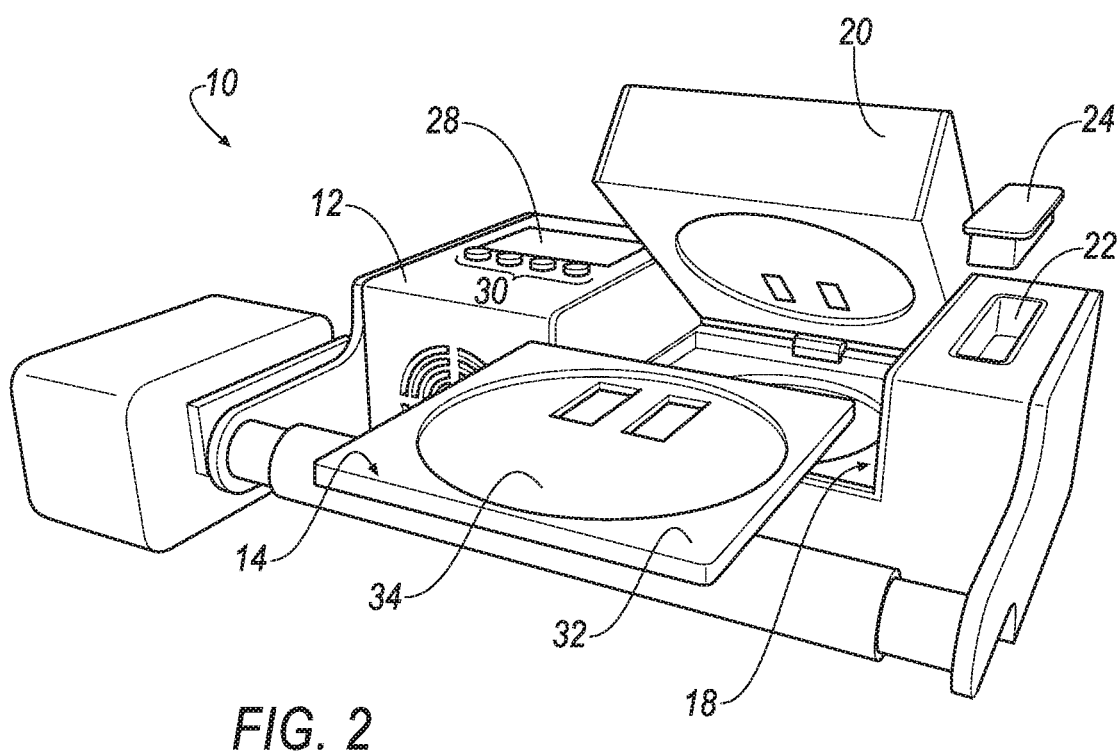
FIG. 2 is a perspective view of the example bio-dosimetry device of FIG. 1 in an open position as well as an example cartridge for performing analysis being received into bio-dosimetry device.
Figure 3:
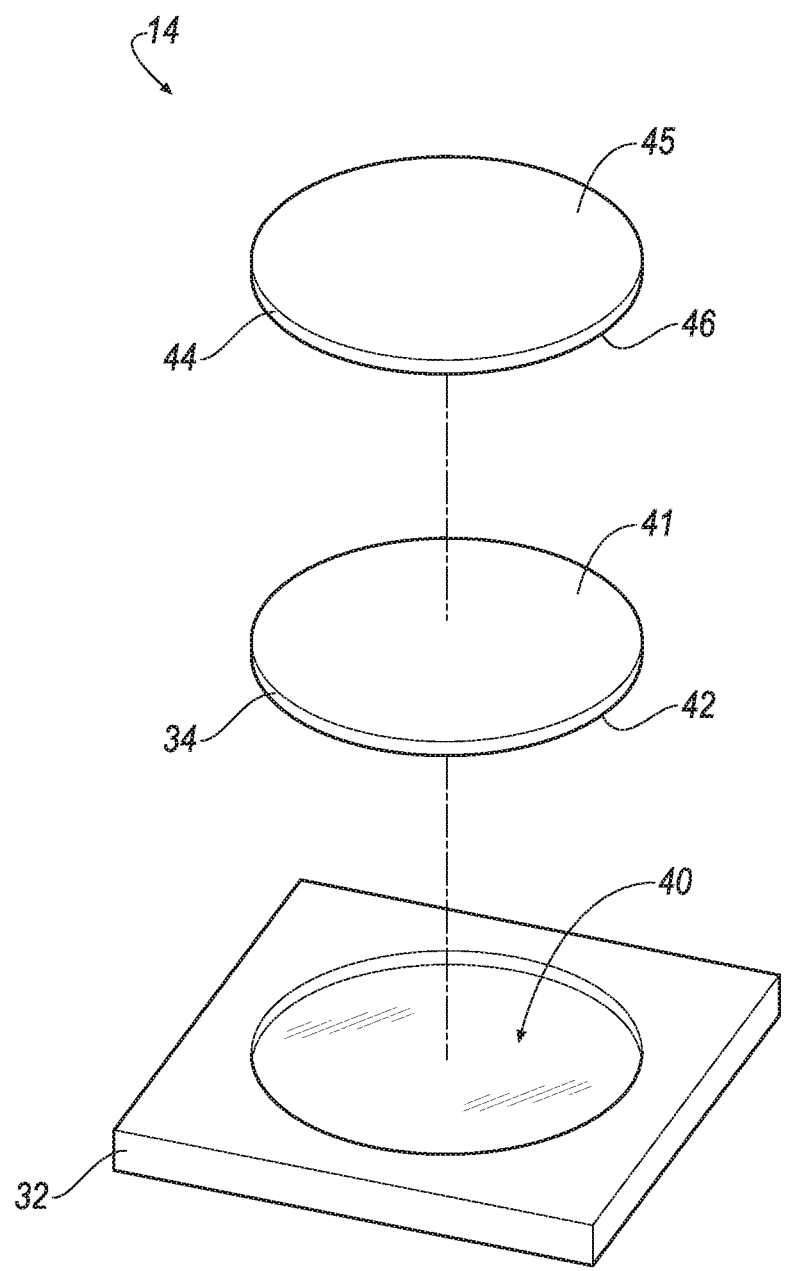
FIG. 3 is an exploded view of the cartridge shown in FIG. 2.

The bio-dosimetry device 12 comprises a housing 16, a socket 18 for receiving the cartridge 14 and a door 20 coupled to the housing 16. The door 20 encloses the socket 18 in a closed position (FIG. 1) and provides access to the socket 18 in an open position (FIG. 2). The housing 16 includes a reservoir 22 for receiving a blood sample and a cap 24 for enclosing the sample within the reservoir 22 (e.g., to avoid contamination). and a handle 26 for carrying the bio-dosimetry device 12. The housing 16 further may include a display 28 for displaying information such as measurement data to a user, and a user input device 30 for receiving input from the user.

The door 20 may be coupled to the housing 16 with a hinge. When the door 20 is the opened position the socket 18 can receive the cartridge 14. Upon receiving the cartridge 14 in the socket 18, the door 20 can be closed. As described below, closing the door 20 can couple components in the bio-dosimetry device 12 to the cartridge 14.

The bio-dosimetry device 12 includes a battery 48 which provides electrical energy to the bio-dosimetry device 12. The battery 48 may be a standard battery such as a lead-acid, nickel-cadmium, lithium-ion battery etc. The battery 48 enables the bio-dosimetry device 12 to be portable and used in locations without access to a power grid.

The bio-dosimetry device 12 further include a computer 50 including one or more processors 52 and one or more memories 54, the memories 54 including instructions for programming the one or more processors 52. The computer 50 executes instructions which can be used carry out the processes for preparing and analyzing the sample for exposure to radiation as described herein. The computer 50 is communicatively coupled to components of the bio-dosimetry device 12 including the display 28, the user input device 30, sensors 56, an illumination system 58, optical detector 60, heating systems 62, pumps 64, blister actuators 66 and a piezo electric element 68.

The display 28 may be, for example, a liquid crystal display (LCD) or organic light emitting diode display (OLED) and can be used for outputting data, for example measurement data, to a user. The display 28 may further be a touch-screen device and used as an input device by the user.

The user input device 30 includes one or more input elements such as buttons, turn knobs, touch-screens, a microphone, etc. that permit a user to input data and/or instructions to the bio-dosimetry device 12.

The sensors 56 can include, for example, temperature sensors, pressure sensors and contact sensors. The sensors 56 can receive instructions from and provide data to the computer 50 to enable the computer 50 to control the processes for preparing and analyzing the samples as described below.

The illumination system 58 provides light for performing PCR. The illumination system 58 is communicatively coupled to the computer 50 and includes a light source. The light source optimally emits light in a narrow band of wavelengths to stimulate the fluorescent tag. The fluorescent tag, in response, emits light at a different wavelength. The band of wavelengths radiated by the light source to stimulate the fluorescent tag needs to be limited to a range that does not overlap the light emitted by the fluorescent tag. There are many possible fluorescent tags (markers) and the wavelength of the light source needs to be matched to the tags. The light sources should be as monochromatic (narrow banded) as possible, such as a laser or a narrow emission light emitting diode or other light source with a narrow notch filter blocking wavelengths outside of the narrow band needed to stimulate the fluorescent tags.

The illumination system 58 may further include electronic circuitry to turn the light source on and off, bias the light source in an operating condition, control or limit the power supplied to the light source, etc. As described below, the illumination system 58 can radiate light on the cartridge 14 during analysis of material to be analyzed, based on commands from the computer 50. Material to be analyzed as used herein is material that has been prepared to be analyzed based on components of the blood sample. The material to be analyzed may include fluorescent markers.

The optical detector 60 is communicatively coupled to the computer 50, and can be, for example, a camera, a charge-coupled device (CCD), a light sensitive, CMOS array, etc. The optical detector 60 may include a filter to block the excitation wavelength (from the light source) used to stimulate a fluorescent tag and allow the fluorescent tag emission through for detection. Following or during illumination of the material to be analyzed by the illumination system 58, the optical detector 60 receives light emitted by the material to be analyzed. The optical detector 60 can provide data to the computer 50 based on the received light. In an example, the material to be analyzed includes fluorescent markers. Following illumination, the fluorescent markers radiate light at a wavelength based on the markers and the optical detector 60 detects the light. In some cases, the optical detector 60 may be used to detect different fluorescent tags emitting light at different wavelengths. In these cases, the optical detector 60 may receive respective images of the two fluorescent tags by applying different filters for each of the respective fluorescent tags.

In at least one example, each of the heating system(s) 62 of the bio-dosimetry device 12 includes a heating element such as a resistance heater and may include electronic circuitry to turn the heating element on and off, bias the heating element in an operating condition, control or limit the power to the heating element, etc. The heating system 62 may further include a sensor 56, such as a temperature sensor, that can be used to detect a temperature of the heating element and provide feedback to the heating system 62 such that the heating system 62 can regulate the temperature of the heating element. As will be explained in greater detail below, the heating system(s) 62 may be used to heat a portion(s) of the cartridge 14 during processing of the blood sample. Further, the heating elements included in the heating system 62 may in some cases be contained in the bio-dosimetry device 12 and in other cases included as part of the cartridge 14.

In at least one example, the pump(s) 64 of the bio-dosimetry device 12 may be electrically coupled to and controlled by the computer 50 such that the computer 50 can turn them on and off. As described in additional detail below, when the cartridge 14 is inserted into the bio-dosimetry device 12, and the door 20 is closed, the pumps 64 may further be in fluid communication with the cartridge 14 such that the pumps 64 can move fluids, e.g., from the reservoir 22 to the cartridge 14 or within the cartridge 14 from one region to another.

The bio-dosimetry device 12 may further include one or more blister actuators 66. Each blister actuator 66 may be communicatively coupled with the computer 50 and include a plunger. The blister actuators 66 may be arranged within the bio-dosimetry device 12 such that, when the cartridge 14 is inserted in the bio-dosimetry device 12 and the door 20 is closed, the blister actuator 66 is within a range of elements on the cartridge 14 such that the plunger, in an extended state, extends into and compresses the elements on the cartridge 14 and releases fluids into a processing flow on the cartridge 14.

The bio-dosimetry device 12 may further include a piezo electric element 38. The piezo electric element 68 may be communicatively coupled with the computer 50 such that it can receive commands, for example, to turn the piezo electric element 68 on and off or adjust a power level of the piezo electric element 68. When the piezo electric element 68 is turned on, it may vibrate at a frequency, for example 20 kHz. When a cartridge 14 is inserted into the bio-dosimetry device 12 and the door 20 is closed, the piezo electric element 68 may be coupled, either directly (in physical contact), or indirectly (for example, via a small air space) with elements on the cartridge 14 and cause the elements to vibrate, transferring mechanical energy to the elements.

The cartridge 14 is a disposable cartridge that is intended to be used to analyze a single blood sample and is configured to be inserted into the bio-dosimetry device 12. The cartridge 14 includes a cassette 32 and a substrate 34. The cassette 32 is adapted to be inserted into the socket 18 of the bio-dosimetry device 12 and includes a recessed area 40 for receiving and supporting the substrate 34. The substrate 34 has a first side 41 and a second side 42 and supports a plurality of sections configured to process and analyze a blood sample and determine a level of exposure to radiation. The cartridge 14 further includes a cover 44 having a first side 45 and a second side 46. The second side 46 of the cover is attached to the first side 41 of the substrate 34 and encloses the processing regions formed in the substrate 34. The substrate 34 and the cover 44 can be made of a material such as glass (e.g., Pyrex), silicon, a silicone-based material, sapphire, a polymer, or any transparent substrate.

The cartridge 14 contains a plurality of regions for processing and analyzing a blood sample to determine a level of exposure to radiation. An overview of the regions of the cartridge 14 will be presented in the next paragraph. Thereafter, the structure and features of different sections of the cartridge 14 will be described in additional detail.

The blood sample is pumped into a lysing region 90 on the cartridge 14, by a micropump 82 or via a port 84. In the lysing region 90, the blood sample is broken into components parts including mRNA. After lysing, the blood sample including the mRNA, is transferred to the binding region 92. In the binding region 92, mRNA from the blood sample is bound (held). The remaining components are removed, by flushing. Thereafter, the bound mRNA in the binding region 92 is flushed with a material, which forms cDNA with the bound mRNA. The cDNA, formed in the binding region 92 is then transferred to a mixing region 94 where the cDNA is more evenly distributed within a reaction mixture. Next, the cDNA is transferred to a polymerase chain reaction (PCR) region 96 where the cDNA is analyzed for exposure to radiation of the mRNA with which the cDNA was previously formed (in the binding region 92).

The micropump 82 may be built into and/or on the substrate 34 and based on a micro-electro-mechanic systems (MEMS) technology. When the cartridge 14 is inserted in the bio-dosimetry device 12 and the door 20 is closed, an input to the micropump 82 may be fluidly coupled to the reservoir 22 in the bio-dosimetry device 12 such that the micropump 82 can pump the sample into the cartridge 14 (for example, into the lysing region 90).

The cartridge 14 may further include one or more ports 84. The ports 84 may be openings formed in the cover 44 of the cartridge 14. The ports 84 may be arranged to fluidly couple, for example, with an outlet of a pump 64 in the bio-dosimetry device 12 when the cartridge 14 is inserted in the bio-dosimetry device 12 and the door 20 is closed. For example, the outlet of the pump 64, which may be a nozzle or a tube, may be inserted into the port 84 when the door 20 of the bio-dosimetry device 12 is closed, such that when the pump 64 is activated, the pump 64 can output a fluid into the port 84.

To store and, at a proper time during the sample processing, inject liquid materials in the processing flow, the cartridge 14 may include one or more blisters 86 fluidly coupled to respective regions in the cartridge 14. For example, one or more blisters 86a may be fluidly coupled to an inlet to the lysing region 90. One or more blister 86b may be coupled to an inlet to the binding region 92 and one or more blister 86c may be coupled to an inlet to the mixing region 94. The blisters 86 may be, for example, a flexible, polymer based, fluid container, that is formed, for example, on a first side 55 of the cover 44.

Microchannels 85 may be used to fluidly couple regions and features of the cartridge 14. For example, a microchannel 85a may couple one or more of the micropump 82, one or more blisters 86a and one or more ports 84 to an inlet of the lysing region. A microchannel 85b may fluidly couple an outlet of the lysing region 90 and an outlet of one or more blisters 86b to an inlet of the binding region 92. A microchannel 85c may couple an outlet of the mixing region 94 to an inlet of the PCR region 96, etc. Each of the microchannels 85 may be formed in the substrate 34 and closed on a first side 41 of the substrate 34 by a second side 46 of the cover 44.

Figure 5:
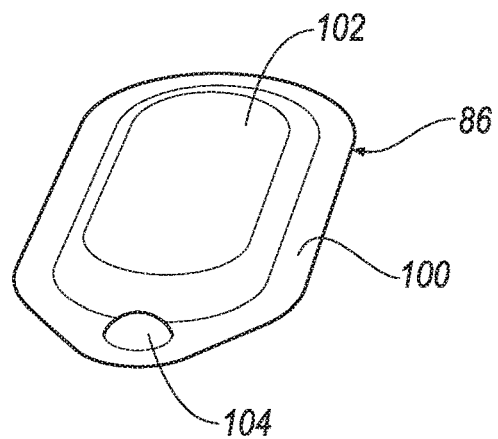
FIG. 5 is a perspective view of an example blister for injecting fluid into the cartridge at points in a processing flow.

An example blister 86 is shown in FIG. 5. The blister 86 may be a hollow, flexible container made of a polymer that forms a cavity for containing a fluid. The blister 86 may have a flat portion 100 for attaching to a surface, for example the first side 45 of the cover 44. The blister 86 may further have a dome-shaped structure 102 arranged on a side of the flat portion and forming the cavity. The dome shaped structure 102 may be, for example, round, or in the form of an elongated rectangle or oval. The blister 86 may have an outlet 104 which may be fluidly coupled, to one of the processing regions on the cartridge 14. The blister 86 is configured such that, when pressure is applied to the dome shaped structure 102, fluid contained in the blister 86 is expelled through the outlet 104.

A blister 86 may be actuated by a blister actuator 66 on the bio-dosimetry device 12. The blister actuator 66 may be arranged in the bio-dosimetry device 12 such that when the cartridge 14 is inserted in the socket 18, the blister actuator 66 is in a range to actuate the blister 86. At an appropriate time during a processing cycle, the computer 50 in the bio-dosimetry device 12 may instruct the blister actuator 66 to extend a plunger toward and apply pressure to the dome-shaped structure 102, and expel the liquid contained in the blister 86 into the processing region to which the blister 86 is fluidly coupled. A size of each blister 86 in the cartridge 14 can be selected based on a volume of liquid required for the processing step in which the blister 86 participates.

An example lysing region 90 is illustrated in FIGS. 6A-6F. The lysing region lyses biological samples by applying ultrasonic stimulation. In an example, the sample to be lysed may be a drop of blood. In other examples, the sample may be any fluid with cells, for example waver with bacteria, cells in lymphatic fluid, cells in urine, etc. The lysing region 90 may also be used for other applications such as lysing microbes, animal and plant cells, fracturing bonds in DNA, RNA, protein aggregates and lipid aggregates. The lysing region 90 may be applied to prepare a sample for polymerase chain reaction (PCR) and rolling circle genetic amplification.

Figure 6A:
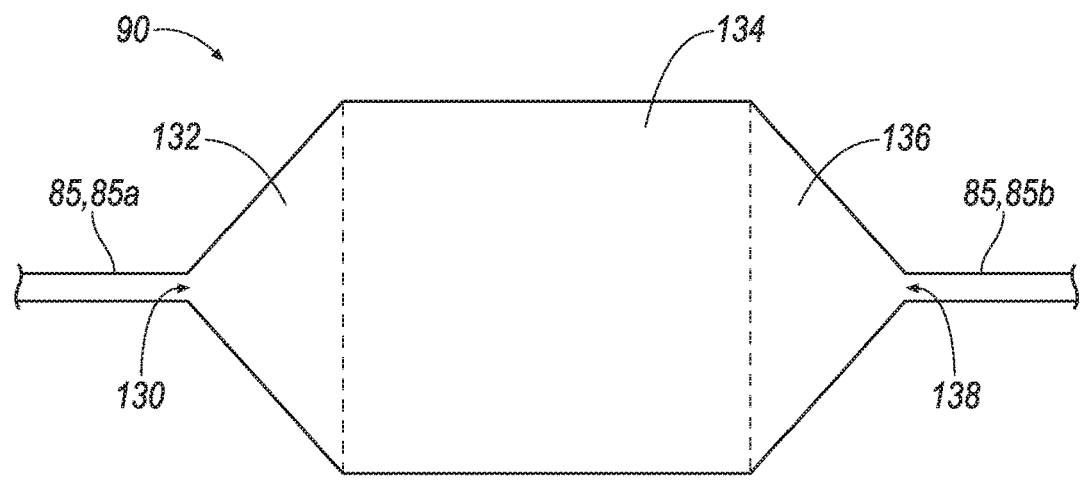
FIG. 6A is a top view of an example lysing region with a cover removed.
Figure 6B:
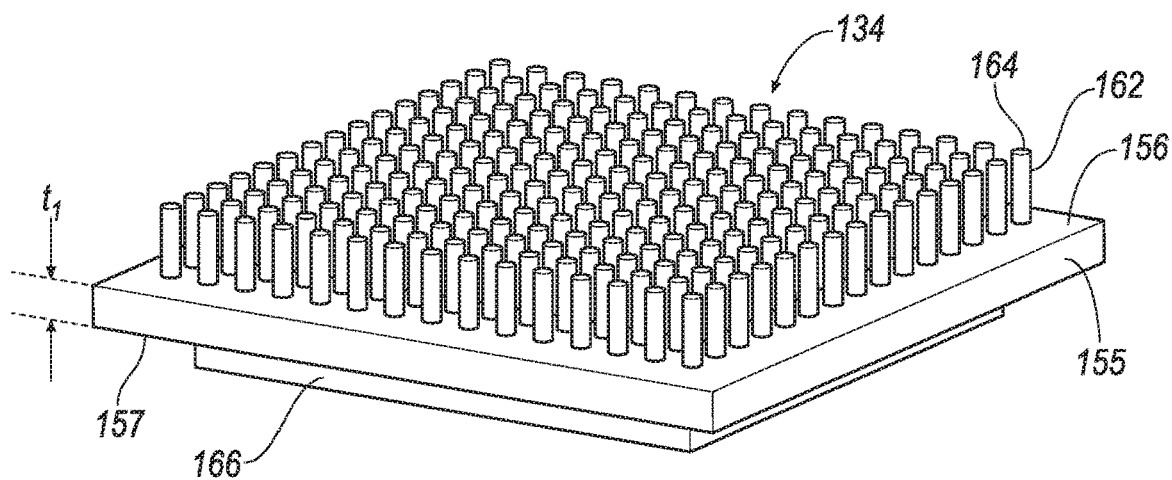
FIG. 6B is a perspective view of an example lysing array with the cover removed.
Figure 6C:
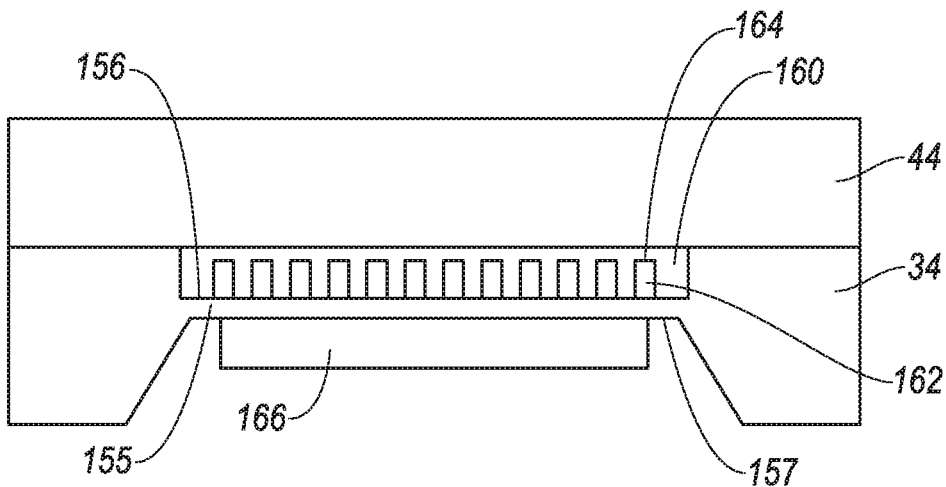
FIG. 6C is a side view of the example lysing array of FIG. 6B showing the cover and including a piezo electric layer.
Figure 6D:
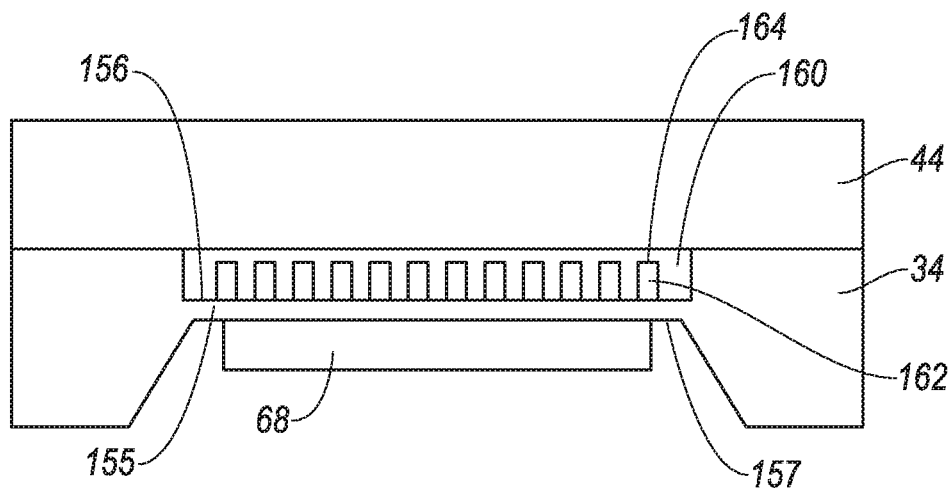
FIG. 6D is a side view of an example lysing array of FIG. 6B showing the cover and including a piezo electric element.

The lysing region 90 includes an inlet 130, a distribution manifold 132, a lysing array 134, an outlet manifold 136, and an outlet 138. The lysing region 90 is configured to receive a sample via the inlet 130, pass the sample through the distribution manifold 132, lyse, by transfer of mechanical energy, the sample into component parts in the lysing array 134 and output the component parts through the outlet manifold 136 to the outlet 138. Each of the inlet 130, the distribution manifold 132, the lysing array 134, the outlet manifold 136 and the outlet 138 can be formed in the substrate 34 (FIGS. 6C, 6D).

The inlet 130 can receive the sample and/or other input material from one or more of the micropump 82, a blister 86 or a port 84, and deliver the sample or input material to the lysing array 134 via the distribution manifold 132. The distribution manifold 132 may be triangular shaped, with an apex of the triangle connected a microchannel 85a delivering the sample and/or input material and a base of the triangle connected to the lysing array 134, such that the distribution manifold 132 broadens from the microchannel 85a to the lysing array 134 to distribute the material across a side of the lysing array 134.

The lysing array 134 may be square and with a typical length of the side in a range from 0.5 cm to 1.0 cm. Other shapes are possible. For example, the lysing array 134 may be rectangular with either a short side of the rectangle of a long side of the rectangle connecting to the distribution manifold. Further, the size of the lysing array 134 is scalable. Increasing the size of the lysing array 134 increases a volume of material that can be lysed in a period of time. A smaller lysing array 134, can be used, for example, to lyse viruses or other small components.

The outlet manifold 136 and outlet 138 output material from the lysing array 134 to a microchannel 85b. The outlet manifold 136 may be triangular shaped with a base of the triangle connected to the lysing array 134 and an apex connected to the microchannel 85b, such that the material output from the lysing array 134 is directed into the microchannel 85b.

The lysing array 134 includes a diaphragm 155 formed in the substrate 34. Referring to FIG. 6B, the diaphragm 155 has a first side 156, a second side 157 and a thickness t1. The thickness t1 can be in a range from 0.01 millimeters to 1 millimeter with a typical value of 0.1 millimeter. Referring to FIG. 6C, the first side 156 of the diaphragm 155, together with the substrate 34 and the cover 44, define a cavity 160. The cavity 160 contains the sample to be lysed during lysing. The cavity 160 may have a typical volume of four microliters and a typical volume range from one to 100 microliters. This range is not intended to be limiting. In addition to cavity volumes within this range, a lysing array 134 according to this disclosure can also have volumes greater than or less than this range.

A plurality of micropillars 162 extend outwardly from the first side 156 of the diaphragm 155 into the cavity 160. Each of the micropillars 162 has a top end 164. In an example, the micropillars 162 are arranged in columns and rows and may be evenly spaced. As an example, the lysing array 134 may include 40 rows and 40 columns of micropillars 162, for a total of 1600 micropillars. The micropillars 162 may be formed, for example, by an embossing or etching process.

The lysing array 134 may include, coupled to the second side 157 of the diaphragm 155, a piezo electric layer 166. During lysing, the piezo electric layer 166 may be stimulated (i.e., an electric current may be applied). Based on the stimulation, the piezo electric layer 166 may apply an oscillating force to the diaphragm 155, causing the diaphragm 155 to flex. At points towards a center of the lysing array 134, the flexing of the diaphragm 155 may be substantially perpendicular to a plane of the diaphragm 155. In an example, the flexing of the diaphragm can result in a displacement in a range from 1 to 20 microns at points towards the center of the lysing diaphragm. In other examples, the displacement can be larger, up to a range of 1 millimeter or more. The amount of displacement may vary with the frequency of stimulation as there is a relaxation time dependent on displacement. That is, a lower frequency of stimulation may result in a larger displacement. The flexing causes a lateral motion on the top ends 164 of the micropillars 162. The lateral motion of the top ends 164 can create a liquid shock wave that can lyse the sample contained in the cavity 160, breaking the sample into component parts. An energy level applied to the diaphragm can be controlled to allow for lysing, for example, of cell walls, without damaging internal organelles in the blood cells.

As an alternative to the piezo electric layer 166, a piezo electric element 68 included in the bio-dosimetry device 12 can be used to stimulate the diaphragm of the lysing region 90. This is illustrated in FIG. 6D. In this case, when the cartridge 14 is inserted in the bio-dosimetry device 12 and the door 20 closed, the piezo electric element 68 is arranged to physically couple with the diaphragm 155 such that when the piezo electric element 68 is turned on, ultrasonic waves radiated from the piezo electric element 68 cause the diaphragm 155 to flex.

Figure 6E:
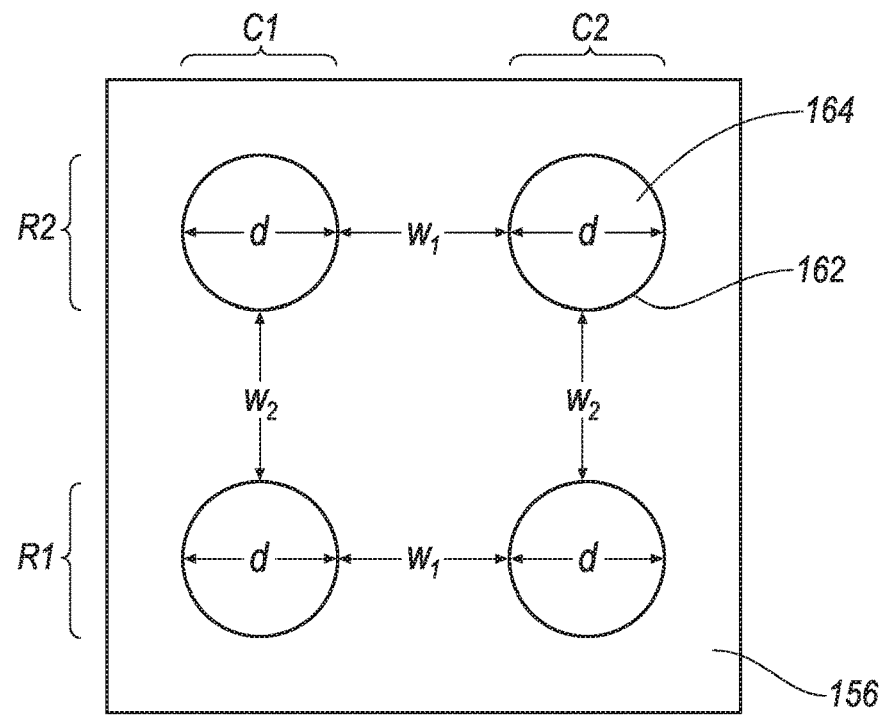
FIG. 6E is a top view of a section of the example lysing array of FIG. 6B with the cover removed.

FIG. 6E is a top view of a section of the lysing array 134, with the cover 44 removed. The section shows two rows R1 and R2 and two columns C1 and C2. The micropillars 162 may be cylindrically shaped, and have a diameter d. The diameter d may, for example, be in a range from 0.01 millimeters to 10 millimeters with a typical value of 0.075 millimeters. The micropillars 162 may be evenly spaced and have a spacing $W_1$ between adjacent micropillars 162 in a row (e.g., the row R1) and evenly spaced and have a spacing $W_2$ between two micropillars 162 in a column (e.g., the column C1). In a typical example, $W_1$ may be substantially equal to $W_2$. The spacings $W_1$ and $W_2$ may be in a range from 0.015 millimeters to 10 millimeters and have a typical value of 0.075 millimeters which is effective for most cells. The ranges of $W_1$ and $W_2$ may be selected based on a particle size of the sample to be lysed and would typically increase as the particle size to be lysed increases.

In another example, the lysing array 134 may be applied to open or break apart protein chains and viruses. In this case, the spacings $W_1$, $W_2$ and the diameter d may be in a range of tens of nanometers.

Figure 6F:
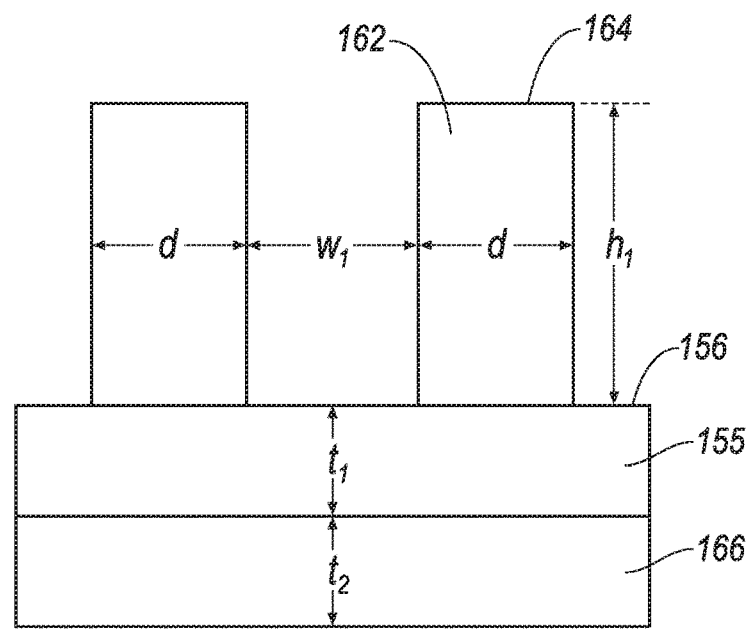
FIG. 6F is a side view of the example the section of the lysing region of FIG. 6E.

FIG. 6F is a side view of the section of the lysing array 134 shown in FIG. 6D. The micropillars 164 can have a height $h_1$. The height $h_1$ can be in a range from 0.1 millimeters to 100 millimeters and can depend on the diameter d chosen for the micropillars 164 and the sample to be lysed. The height $h_1$ and diameter d are typically selected such that an aspect ratio $h_1/d$ is 10, with a range from 5 to 20. For example, in the case that the diameter d is selected to be 2 millimeters, the height $h_1$ can be selected to be 20 millimeters.

The diaphragm 155 has a thickness $t_1$. As noted above, the thickness $t_1$ can be in the range 0.01 millimeters to 1 millimeter with a typical value of 0.1 millimeters. The thickness of the piezo electric layer 166 (when present) may be in a range from 0.1 millimeters to 10 millimeters.

Other shapes may be used for the cross-section of the micropillars 162. For example, the cross-section may be rectangular or triangular, the micropillars 164 may be conical with a base of the cone located at the first side 156 of the diaphragm 155, etc.

FIGS. 7A-7D illustrate an example binding region 92. The binding region 92 includes a microchannel 200 having an inlet 203 and an outlet 204. During operation, material, for example, a lysed blood sample flows through the microchannel 200 in a direction 212.

Figure 7A:
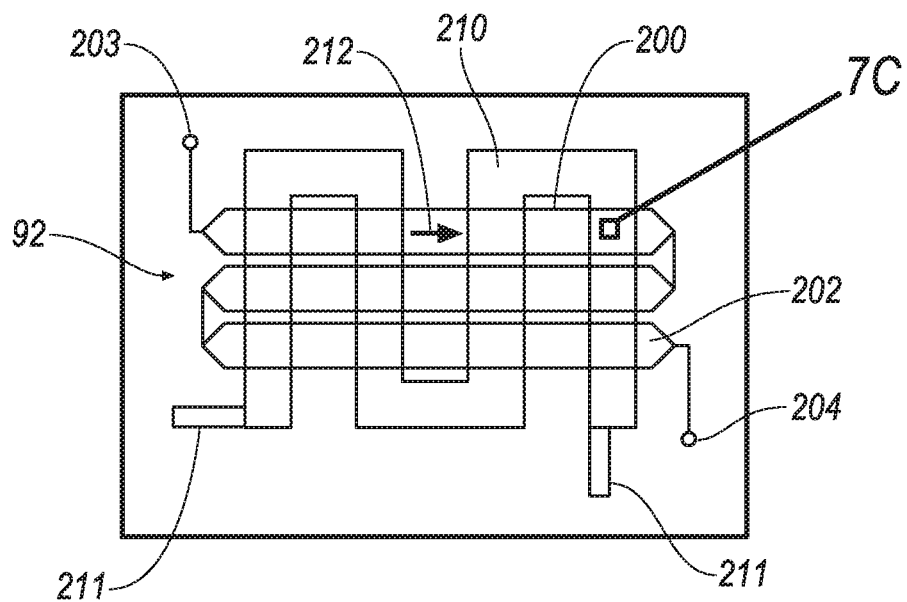
FIG. 7A is a top view of an example binding region.
Figure 7B:
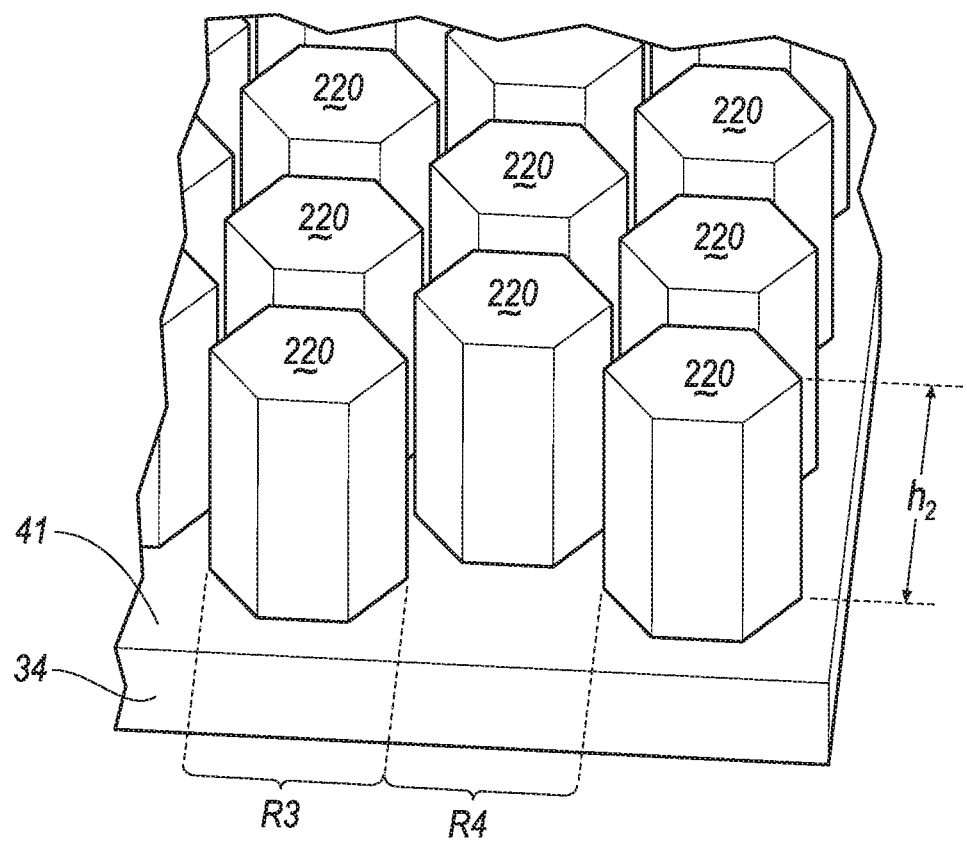
FIG. 7B is a perspective view of a section of the stationary phase in the binding region of FIG. 7A.
Figure 7C:
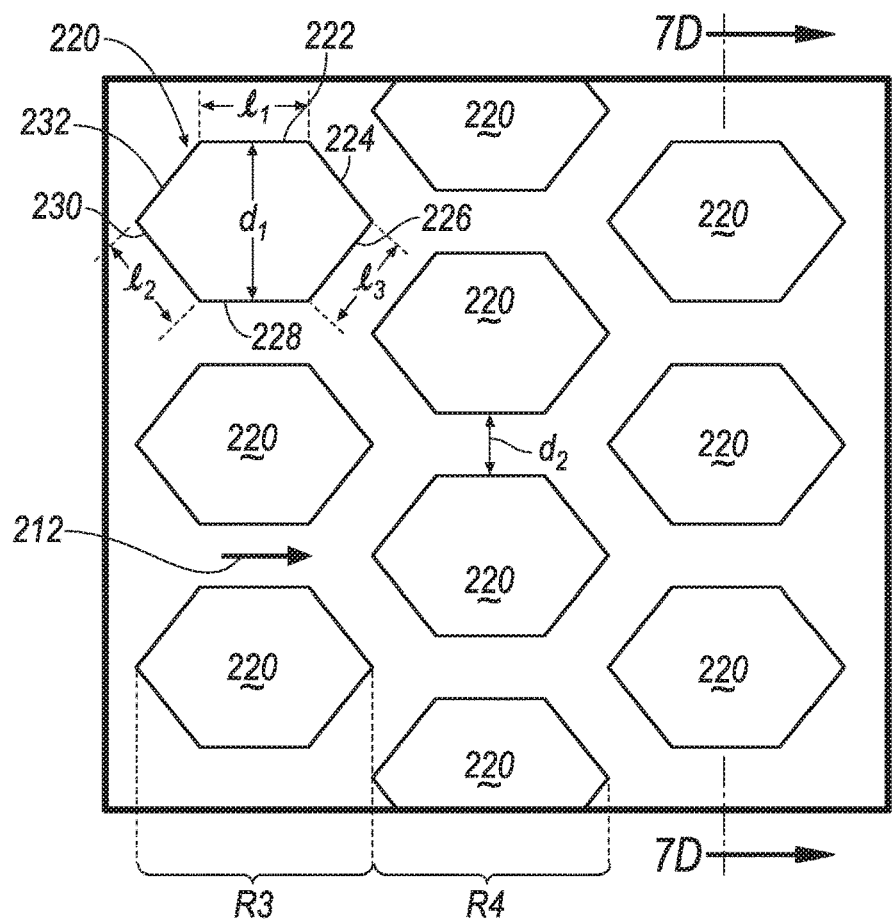
FIG. 7C is a top view of a section of the stationary phase in the binding region of FIG. 7A.
Figure 7D:
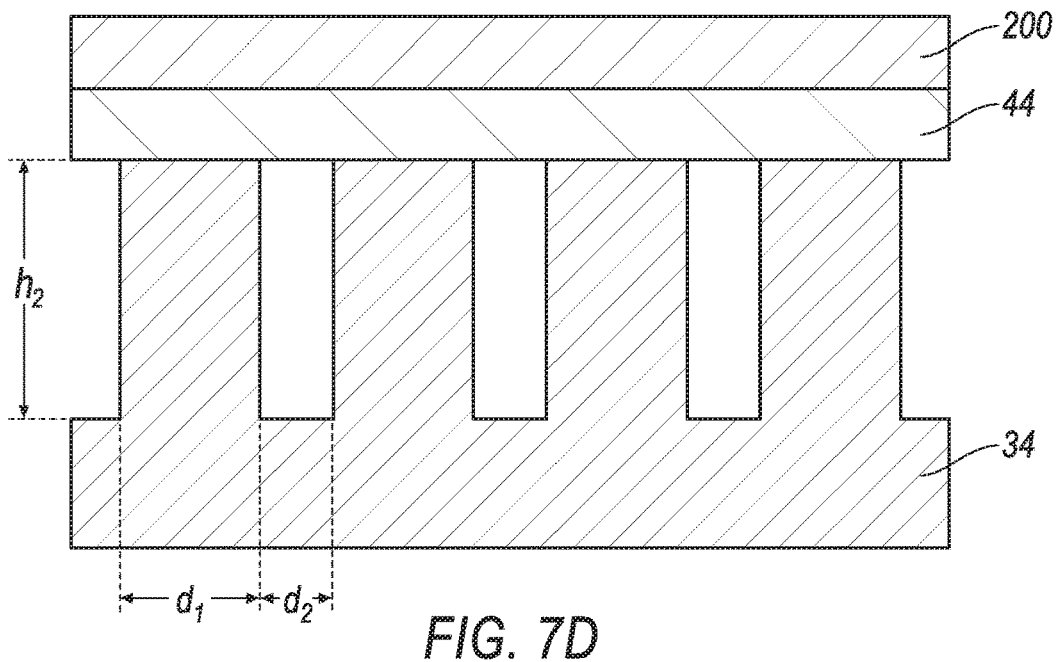
FIG. 7D is a side view of a section of the stationary phase in the binding region of FIG. 7A.

The microchannel 200 includes a stationary phase 202. The stationary phase 202 includes a plurality of micropillars 220. The micropillars 220 are formed in and extend outwardly from the substrate 34. As shown in FIGS. 7B and 7C, the micropillars 220 are arranged in rows, for example rows R3 and R4. Each row is offset from a previous row such that the micropillars 220 in the row R4 are arranged to correspond with an opening between micropillars 220 in the row R3.

As an example, as shown in FIG. 7C, the micropillars 220 may have a cross-section having a hexagonal shape. The micropillar 220 has first, second, third, fourth, fifth and sixth sides 222, 224, 226, 228, 230 and 232. First and fourth sides 222, 228 are parallel, and have a length $l_1$. Second and fifth sides 224, 230 are parallel and have a length $l_2$. Third and sixth sides 226, 232 are parallel and have length $l_3$. In an example, the micropillar 220 has a diameter $d_1$ and a spacing between the micropillars $d_2$. The diameter $d_1$ may be in a range of two microns to 2,000 microns, with a typical value of 20 microns. The spacing may be in a range from one micron to 1,000 microns, with a typical value of 10 microns. The micropillars 220 have a height $h_2$. The height $h_2$ may be in a range of 10 microns to 10 millimeters, with a typical height of one millimeter.

In some cases, the micropillars 220 may be coated with a binding material to bind target components of the sample. For example, in the case of a blood sample containing mRNA, the micropillars 220 may be coated with oligo dT25 to bind the mRNA in the blood sample to the micropillars 220.

The binding region 92 further may include a heating element 210 having two contacts 211 on opposite ends. The heating element 210 may be supported on the cover 44. The heating element 210 may be formed of a resistive material such that, when an electrical voltage is applied across the two contacts 211, a current will flow through the heating element 210 and generate heat.

Additionally or alternatively, during operation of the bio-dosimetry system 10, a heating system 62 in the bio-dosimetry device 12 may be arranged such that when the cartridge 14 is inserted into the socket 18 and the door 20 closed, the heating system 62 is thermally coupled to (i.e., can heat) the binding region 92.

The binding region 92 can be used to bind mRNA in a blood sample to the stationary phase 202. This is described below as the process 1600 in reference to the FIG. 16.

The binding region 92 can further be used to convert the mRNA, bound in the stationary phase, to cDNA. This is described below as the process 1700 in reference to the FIG. 17.

Figure 8A:
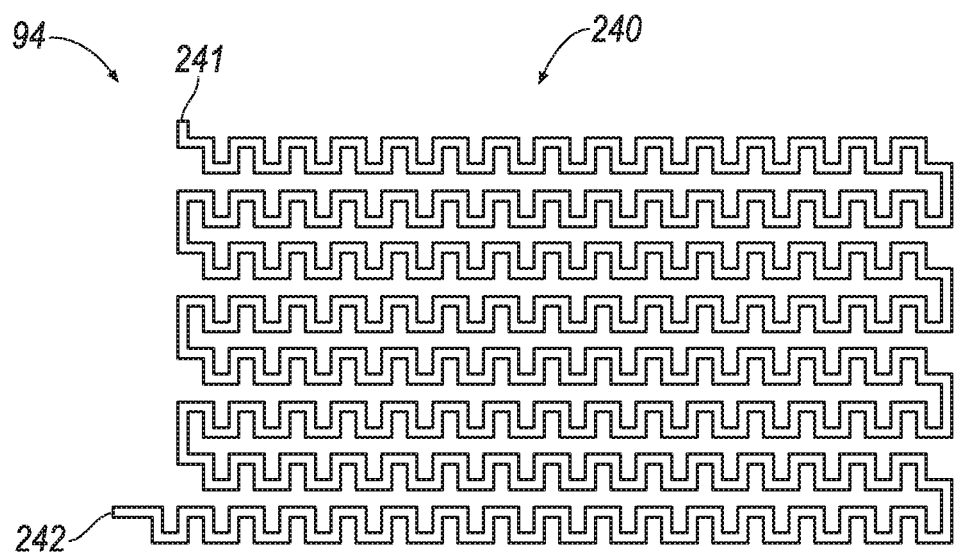
FIG. 8A is a top view of an example mixing region.
Figure 8B:
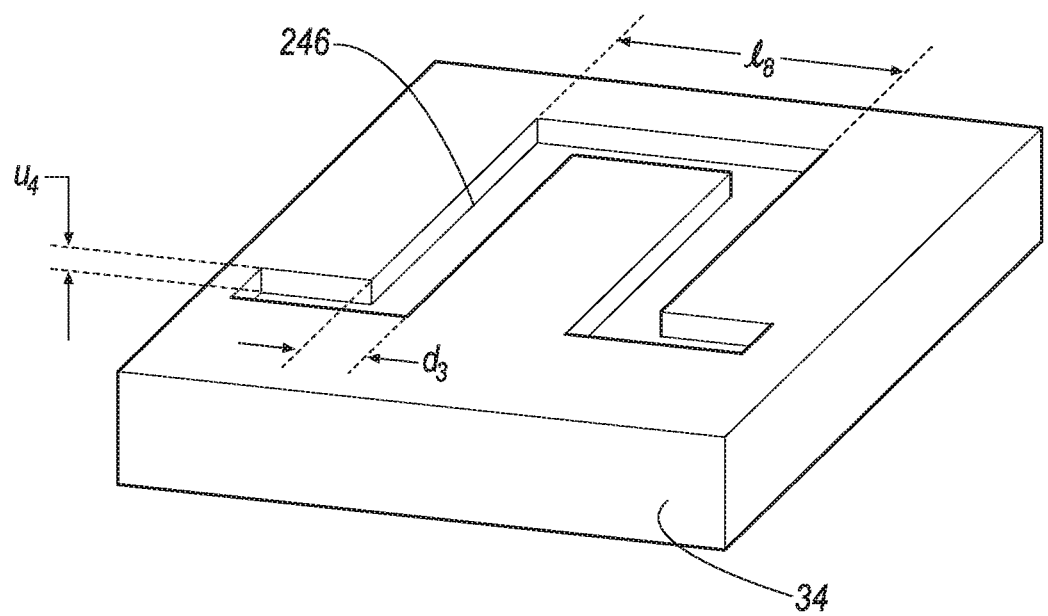
FIG. 8B is a perspective view of a portion of the mixing region of FIG. 8A.

FIGS. 8A and 8B illustrate the mixing region 94. The mixing region 94 includes a microchannel 240 having an inlet 241 and an outlet 242. The microchannel 240 may be in the form of a meander having straight portions coupled at angles of, for example, 90° to one another. A length 18 of a straight portion in the meander may have a typical value of 1 millimeter to 2 millimeters. The microchannel 240 is formed in the substrate 34 and has a width $d_3$. The width $d_3$ can be in a range of 0.1 millimeters to 2 millimeters with a typical value of 0.5 millimeters. The depth $U_4$ of the microchannel 240 can be in a range from 0.1 millimeters to 1 millimeter with a typical value in a range from 0.1 to 0.2 millimeters.

The microchannel 240 can be used to remove gradients of cDNA in reaction mixture. The reaction mixture, containing the cDNA may enter the mixing region 94 at the inlet 241, pass through the microchannel 240, continue through the outlet 242. As the reaction mixture containing the cDNA passes through the microchannel 240, the changes of directions as the microchannel 240 passes through the 90 passing through 90° angles, may cause turbulence in the fluid flow, mixing the cDNA within the reaction mixture. Through the mixing process, the cDNA may be more evenly distributed, reducing or eliminating gradients in the cDNA within the reaction mixture.

The mixing region 94 may have other shapes or features. For example, the width $d_3$ of the microchannel 240 may be varied alternatively between a first width and a second width or the depth $U_4$ of the microchannel 240 varied alternatively between a first depth and a second depth to create turbulence in the reaction mixture flow. As another example, extensions or bumps may be formed, extending from a bottom of the microchannel 240 into the microchannel 240 to increase turbulence in the reaction mixture flow.

Figure 9:
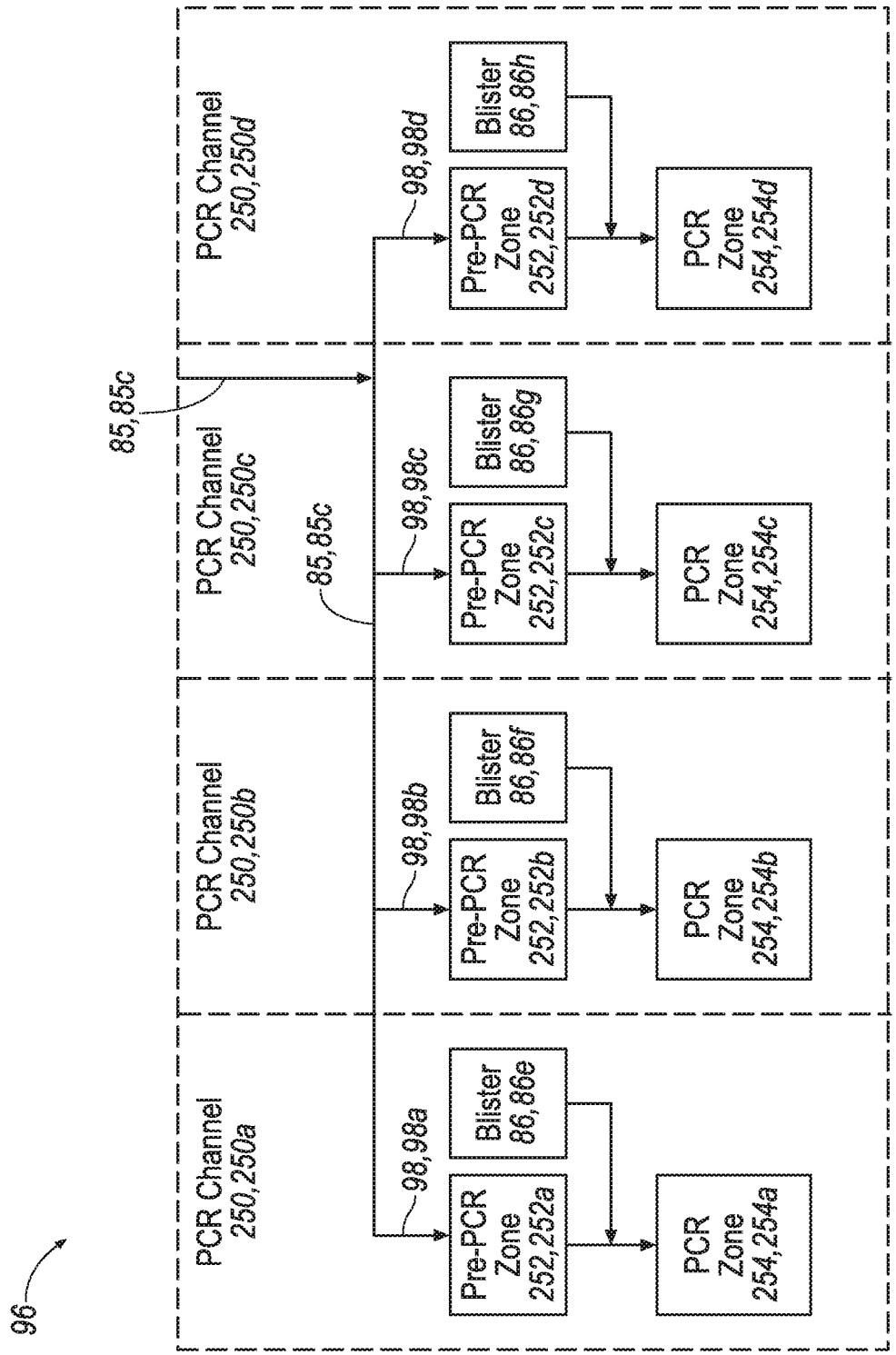
FIG. 9 is a block diagram of an example PCR region.

FIG. 9 is a diagram of an example PCR region 96. The PCR region 96 receives material including cDNA from the mixing region 94. The PCR region analyzes the cDNA for exposure to radiation of the mRNA from which the cDNA was generated. Analyzing the cDNA includes thermally cycling the material to be analyzed including the cDNA between two temperatures, as described below. The PCR region 96 receives the material via a microchannel 85c. The microchannel 85c couples the mixing region 94 (FIG. 4) via four sub-microchannels 98a, 98b, 98c, 98d to four respective PCR channels 250a, 250b, 250c, 250d.

A PCR region 96 including four PCR channels 250a, 250b, 250c, 250d is only an example. The PCR region 96 may include any number of PCR channels 250.

As shown in FIG. 9, the first PCR channel 250a includes the pre-PCR zone 252a, the blister 86e and the PCR zone 254a, the second PCR channel 250b includes the pre-PCR zone 252b, the blister 86f and the PCR zone 254, the third PCR channel 250c includes the pre-PCR zone 252c, the blister 86g and the PCR zone 254c and the fourth PCR channel 250d includes the pre-PCR zone 252d, the blister 86h and the PCR zone 254d. The four PCR channels 250a, 250b, 250c, 250d may be the same or similar, and will be described as an example PCR channel 250 including an example pre-PCR zone 252, an example blister 86 and an example PCR zone 254 below.

Figure 10:
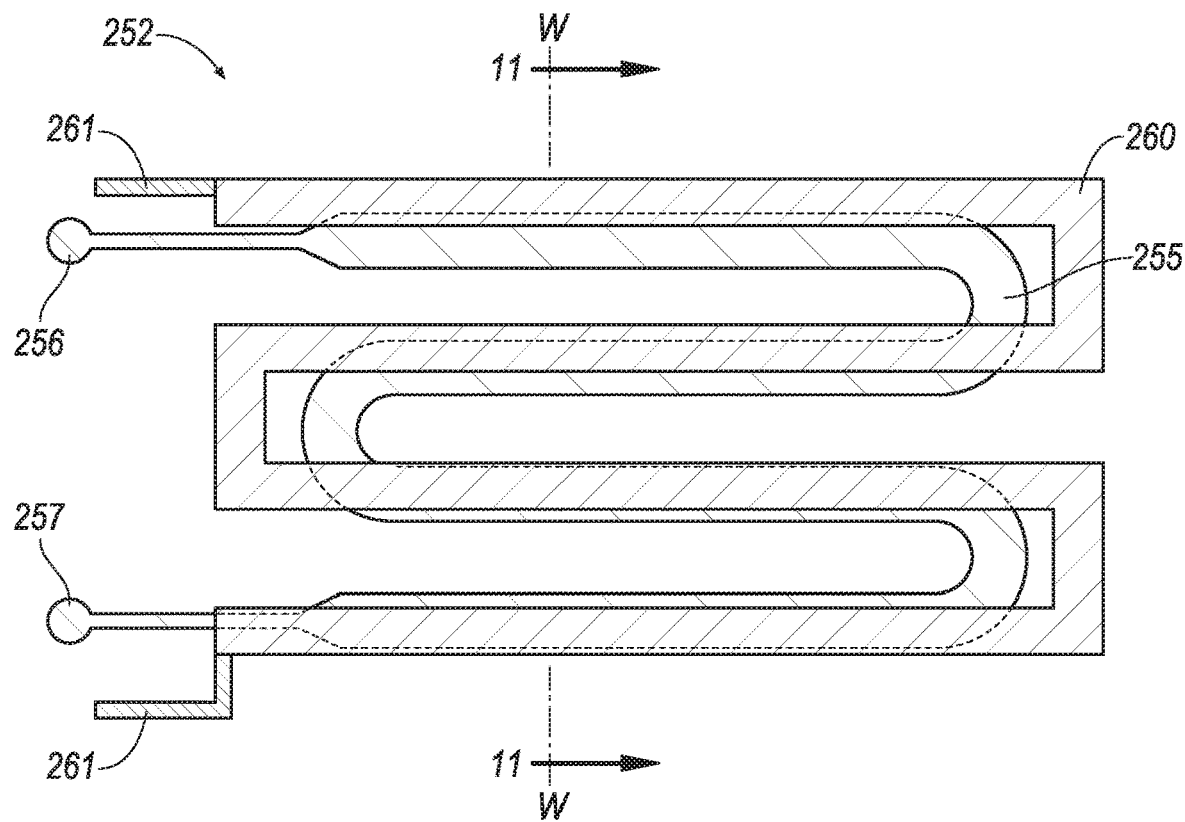
FIG. 10 is a top view of an example pre-PCR zone.
Figure 11:
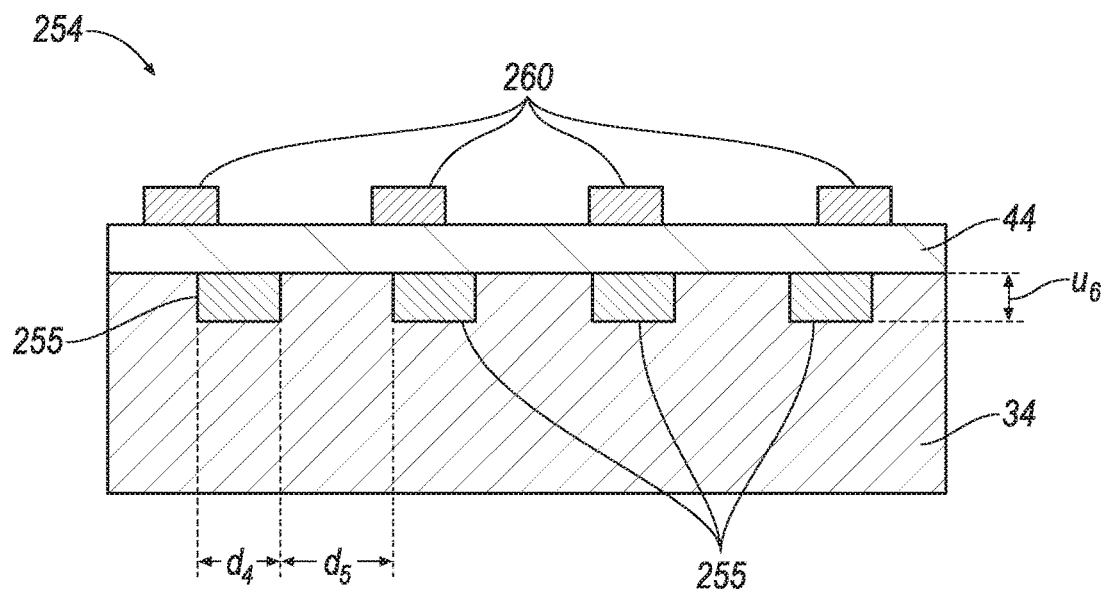
FIG. 11 is side view of the example pre-PCR zone of FIG. 10 along an axis WW.

FIGS. 10 and 11 illustrate an example pre-PCR zone 252. The pre-PCR zone 252 heats material prior to beginning analysis in the PCR zone 254. The pre-PCR zone 252 includes a microchannel 255 including an inlet 256 and an outlet 257. Material enters the microchannel 255 at the inlet 256 and flows towards the outlet 257. The outlet 257 may be coupled, for example, to a sub-microchannel 98 such as the sub-microchannel 98a. The outlet 257 may be coupled to the PCR zone 254.

The microchannel 255 may have a width $d_4$ and a depth $U_6$. Adjacent parallel sections of the microchannel 255 may be spaced away from each other by a distance $d_5$. The width $d_4$ may be in a range from 0.1 millimeters to 2 millimeters with a typical value of 1 millimeter. The depth $U_6$ of the microchannel 255 may be in a range from 0.05 millimeters to 2 millimeters with a typical value of 1 millimeter. The spacing $d_5$ between adjacent sections of the microchannel 255 may have a range from 0.1 millimeters to 5 millimeters with a typical value of 2 millimeters.

The pre-PCR zone 252 further may further include a heating element 260 including two contacts 261. on opposite ends. The heating element 260 may be supported on the cover 44. The heating element 260 may be formed of a resistive material such that, when an electrical voltage is applied across the two contacts 261, a current will flow through the heating element 260 and generate heat.

Additionally or alternatively to including the heating element 260, a heating system 62 in the bio-dosimetry device 12 may be arranged such that when the cartridge 14 is inserted into the socket 18 and the door 20 closed, the heating system 62 thermally couples to (i.e., can heat) the pre-PCR zone 252.

FIGS. 12A through 12F illustrate an example PCR zone 254. The PCR zone 254 thermally cycles the material between a first temperature and a second temperature, and then images the material using fluorescent markers. The imaging provides data indicating a degree of exposure to radiation of the original sample.

Figure 12A:
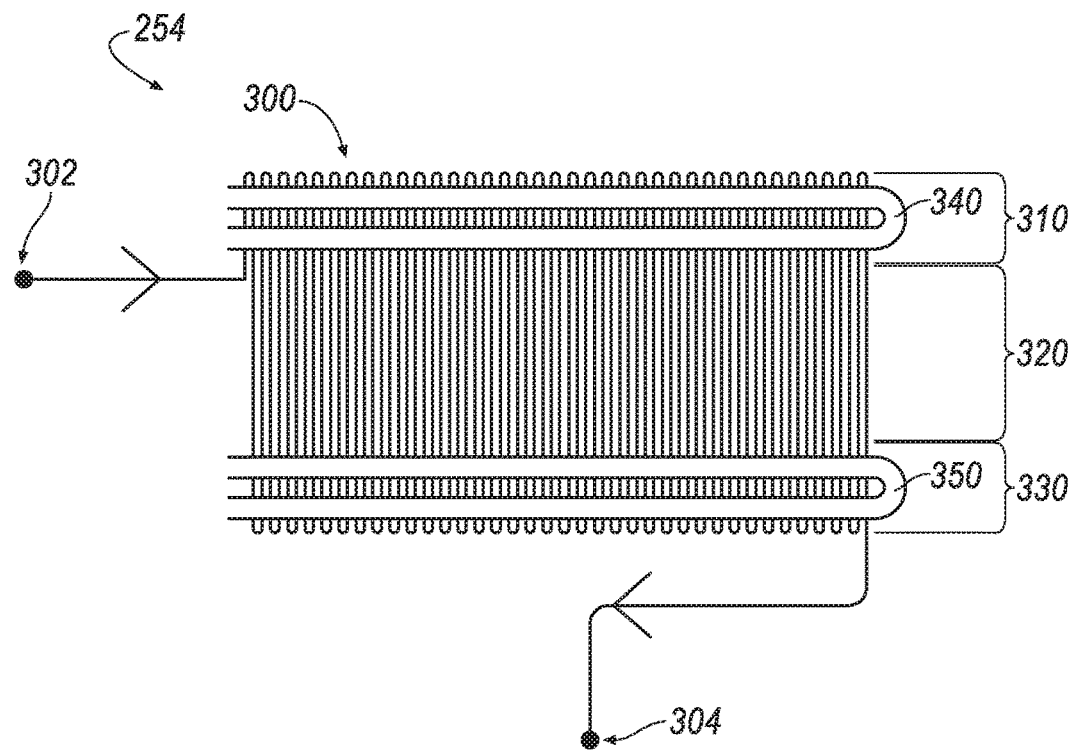
FIG. 12A is a top view of an example PCR zone.
Figure 12B:
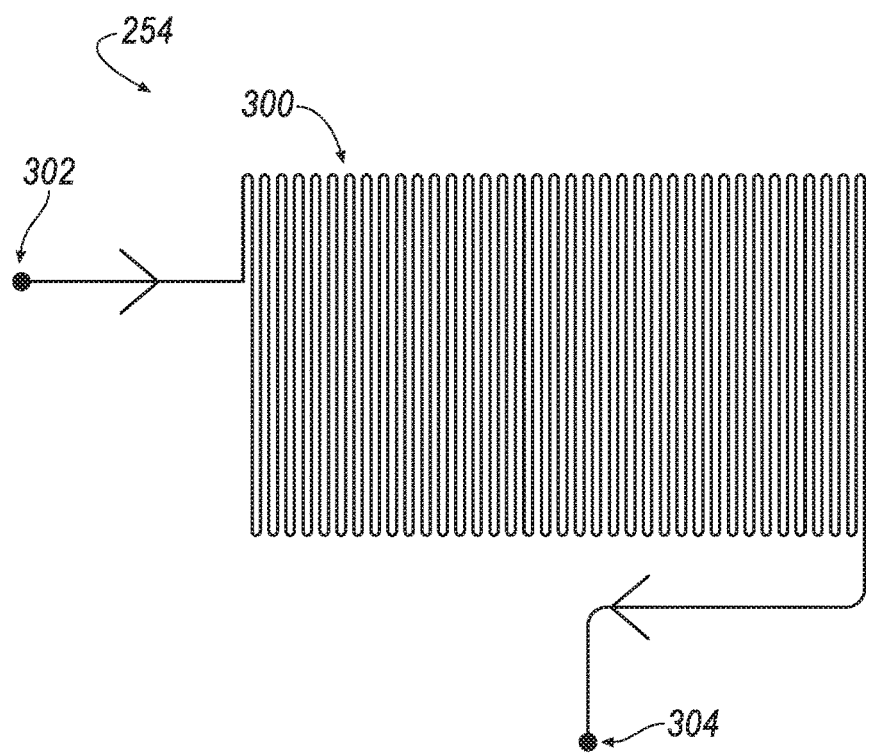
FIG. 12B is a top view of the example PCR zone of FIG. 12A with the heating elements removed.

The PCR zone 254 includes a microchannel 300. As shown in FIG. 12A, the microchannel 300 meanders from an inlet 302 to an outlet 304. In practice, material to be analyzed by the PCR zone 254 is pumped into the inlet 302 and flows through the microchannel 300 to the outlet 304.

The PCR zone 254 includes a first heating region 310, a detection region 320 and a second heating region 330. One or more first heating elements 340 may extend across the first heating region 310. Similarly, one more second heating elements 350 may extend across the second heating region 330. The first and second heating elements 340, 350 may be arranged on and supported by the cover 44.

The first and second heating regions 310, 330 are spaced away one from the other, to eliminate or reduce thermal interference between the first and second heating regions 310, 330. That is, maintaining the first heating region 310 at a first temperature should not interfere with maintaining the second heating region 330 at a second temperature, and vice versa.

In an example, the detection region 320 is arranged between the first heating region 310 and the second heating region 330. The detection region 320 is characterized in that there are no heating elements organized above the microchannel 300. Other arrangements of the detection region 320, are possible. However, placing the detection region 320 between the first and second heating regions 310, 330 has the advantage of efficient use of the space required for separating the first and second heating regions 310, 330.

Additionally or alternatively to the first and second heating elements 340, 350, a heating system 62 included in the bio-dosimetry device 12 can be used respectively to heat each of the first the second heating regions 310, 330.

The microchannel 300 is formed of a plurality of interconnected segments 303 (FIG. 12C) each segment 303 is arranged to perform one thermal cycle on the material flowing through the microchannel 300. One thermal cycle is defined as passing through the first heating region 310 followed by passing through the second heating region 330. Typically, in a PCR zone 254, the microchannel 300 may include approximately 35 segments 303. The number of segments 303 can be adjusted, based on the specific analysis to be performed in the PCR zone 254.

Figure 12C:
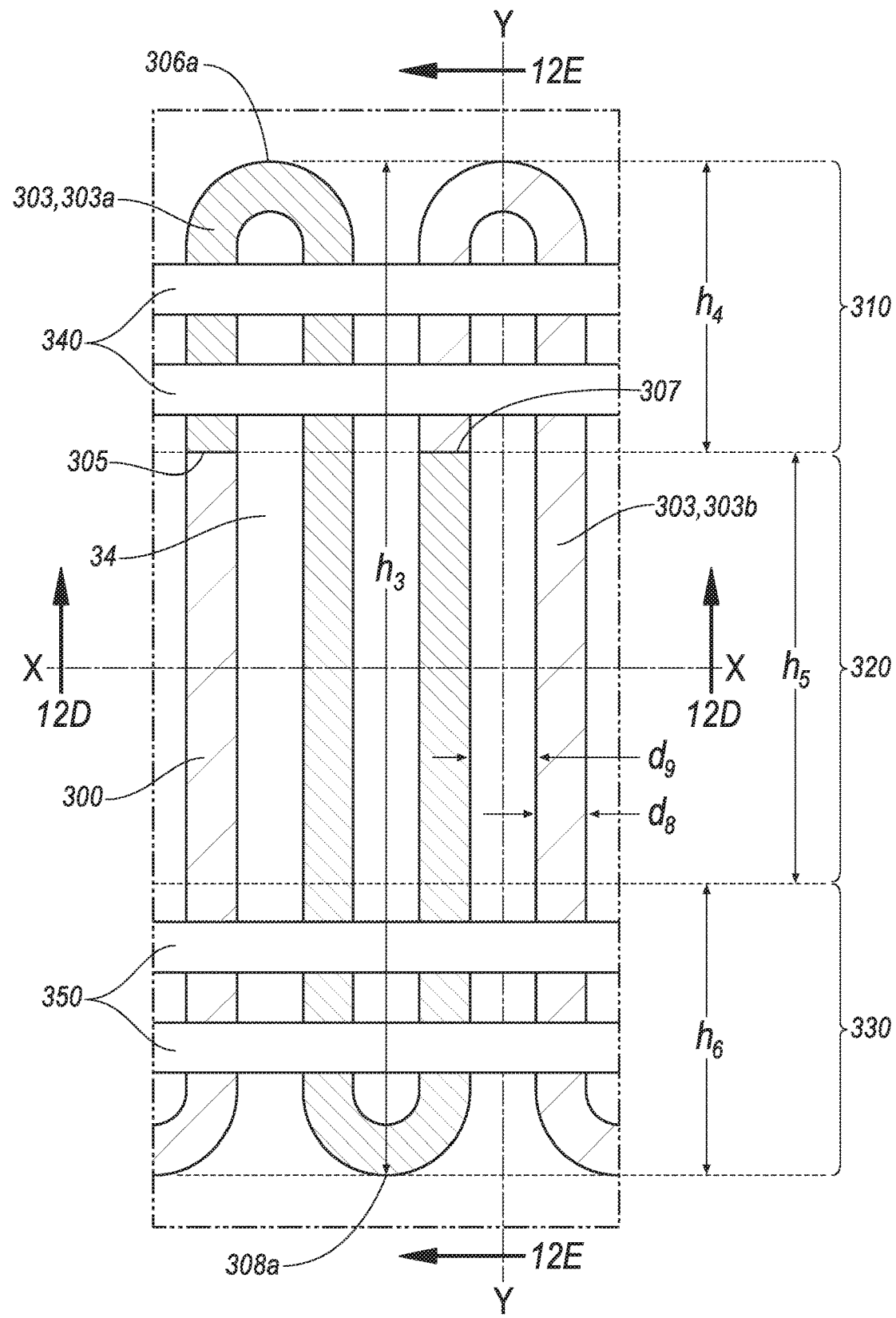
FIG. 12C is a top view of a section of the PCR zone of FIG. 12A.

FIG. 12C is an enlarged view of a section of the microchannel 300 illustrating an example segment 303a. The segment 303a has a first end 305 and a second end 307. The segment 303a starts at the first end 305, continues through the first heating region 310, through the detection region 320, through the second heating region 330 and back through the detector region to the second end 307. The microchannel 300 then continues in a next segment 303b. As described below, when performing PCR, the first heating region 310 will be maintained at a first temperature and the second heating region 330 will be maintained at a second temperature, so that, as the material to be analyzed passes through the microchannel 300, it is repeatedly cycled between the first temperature and the second temperature.

As shown in FIG. 12C, the microchannel 300 has a width $d_8$. The width $d_8$ can be in a range from 0.01 millimeters to 1 millimeter with a typical value of 0.05 millimeters. The width $d_8$ can be selected depending on a volume of fluid to be passed through the microchannel 300, a particle size of the fluid passing through the microchannel 300, the manufacturing process used to create the microchannel 300 in the substrate 34, etc.

The microchannel 300 further has a spacing $d_9$ between parallel portions of microchannel 300. The spacing $d_9$ can be in a range from 0.01 millimeters to 3 millimeters with a typical value of 1 millimeter and can depend on factors such as the manufacturing process used to create microchannel 300. To conserve space in the substrate, the spacing $d_9$ will typically be chosen to be close to or equal to a minimum feature size allowed by the manufacturing process used to form the microchannel 300 in the substrate 34.

The microchannel 300 further has a height $h_3$. The height $h_3$ is the distance, as measured along the axis Y-Y, from a furthest extension of the microchannel 300 within the first heating region 310, for example the point 306a, to a furthest extension of the microchannel 300 within the second heating region 330, for example the point 308a.

As further illustrated in FIG. 12C, the first heating region 310 has a height $h_4$. The detection region 320 has a height $h_5$ and the third heating region 330 has a height $h_6$. The height $h_3$ of the microchannel 300 is equal to the sum of the height $h_4$ of the first heating region 310, the height $h_5$ of the detector region and the height $h_6$ of the second heating region 330. That is, $h_3 = h_4 + h_5 + h_6$.

The height $h_4$ of the first heating region 310 can be determined, for example, by the area required for the first heating element 340, based on the target first temperature of the first heating region 310. Similarly, the height $h_6$ of the second heating region 330 can be determined by the area required for the second heating element 350, based on the target second temperature for the second heating region. The height $h_5$ of the detection region 320 can be determined, for example, based on having a specifically defined region for detecting (counting) cDNA based on a tag emission. The sensitivity of the detection increases as an area of the detection region 320 increases. Further, as described above, in the case that the detection region 320 is located between the first heating region 310 and the second heating region 330, the height $h_5$ can be determined based on a distance required to thermally isolate the first heating region 310 from the second heating region 330.

Figure 12D:
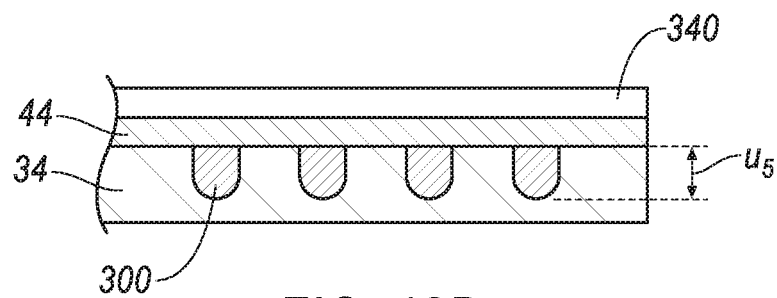
FIG. 12D is a side view along cross-section X-X of the section of the example PCR zone of FIG. 12C.

FIG. 12D is a partial side view of a section of the PCR zone 254 shown in FIG. 12C, cut along the axis X-X. The microchannel 300 is formed in the substrate 34. The cover 44 is attached to the substrate 34, forming a top of the microchannel 300. The microchannel 300 has a depth $U_5$. The depth $U_5$ can be in a range from 10 microns to 1000 microns, with a typical value of 100 microns.

Figure 12E:
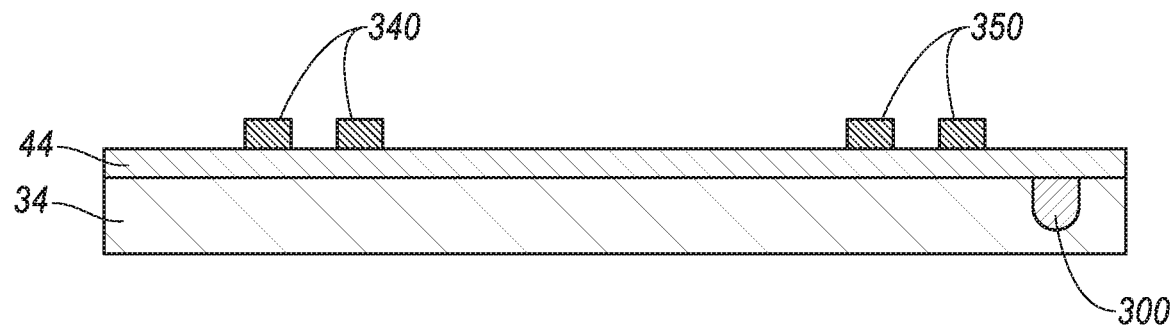
FIG. 12E is a side view along cross-section Y-Y of the section of the example PCR zone of FIG. 12C.

FIG. 12E is a partial side view of a section of the PCR zone 254 shown in FIG. 8C, cut along the axis Y-Y. As above, the microchannel 300 is formed in the substrate 34 and covered by the cover 44. First and second heating elements 340, 350 are arranged on and supported by the cover 44.

Figure 12F:
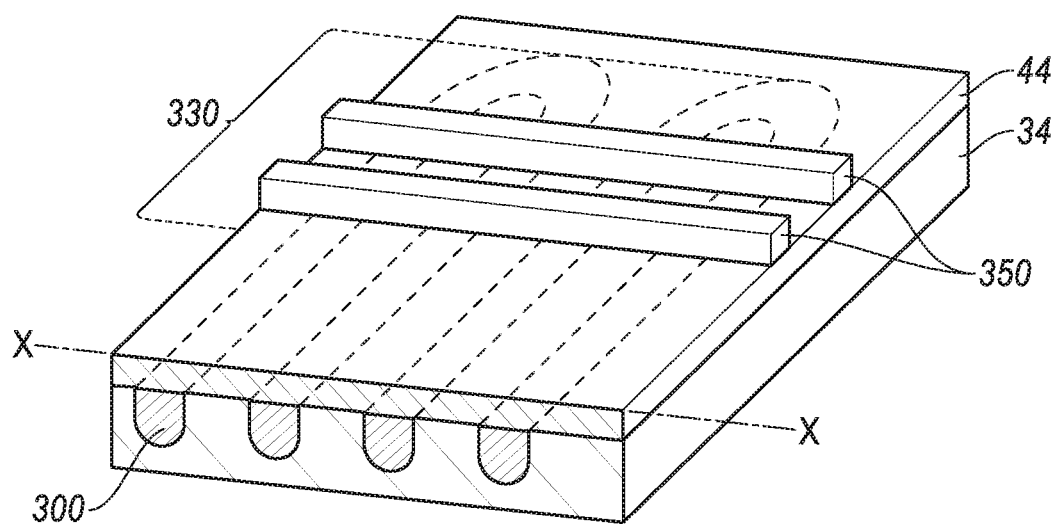
FIG. 12F is a perspective view of the section of the example PCR zone of FIG. 12C.

FIG. 12F is a partial perspective view of the section of the PCR zone 254 shown in FIG. 12D. The microchannel 300 is shown extending through the second heating region 330 and back again with each segment of the microchannel 300.

In an example, the pre-PCR zone 252 may be physically arranged on the substrate 34 near (e.g., adjacent) the PCR zone 254 in the same PCR channel 250. More specifically, the pre-PCR zone 252 may be arranged near the first heating region 310 of the PCR zone 254. This allows the pre-PCR zone 252 to be heated to a substantially same temperature as the temperature of the first heating region of the PCR zone 254. The heating element 260 in the pre-PCR zone 252 may be electrically coupled to the first heating element 340 in the first heating region. In a case that the heating system 62 is used to heat the first heating region 310, the same heating system 62 can also be used to heat the pre-PCR zone 252.

Figure 13:
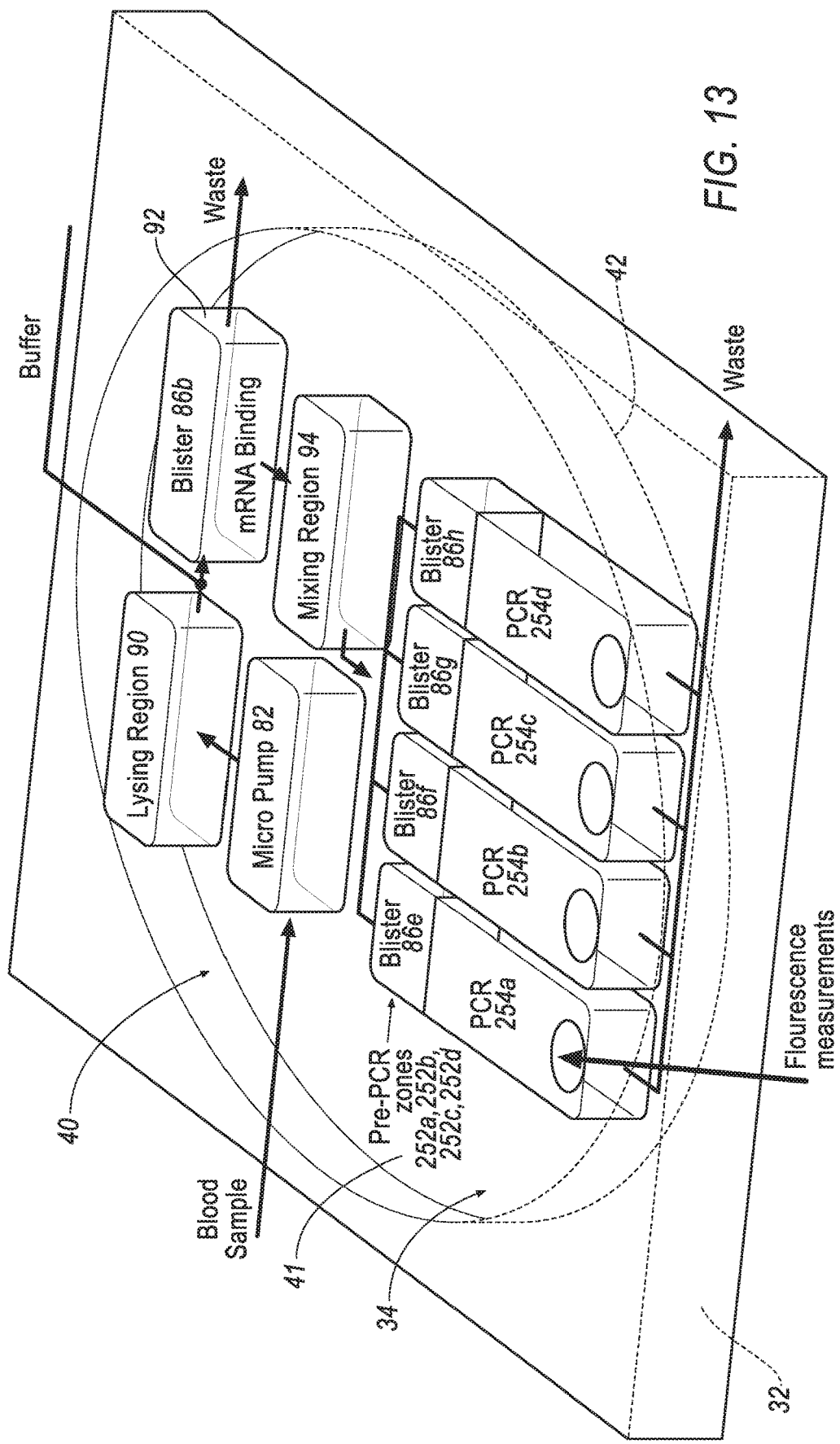
FIG. 13 is an illustration of an example arrangement of a cartridge 14.

FIG. 13 illustrates an example organization of a cartridge 14. A cassette 32 supports a substrate 34 in a recessed area 40. The substrate 34 has a first side 41 and a second side 42. A micropump 82 receives a blood sample and pumps the blood sample to the lysing region 90. After performing lysing on the blood sample, the lysing region 90 outputs the lysed blood sample to the binding region 92. A blister 86b is arranged above the binding region 92, which may be used to inject fluid, for example, a reaction material for conversion of the mRNA to cDNA in the binding region 92. A single blister 86b is only an example. One or more blisters 86b may be used to inject fluid into the binding region 92. The binding region 92 outputs material including cDNA to the mixing region 94. In the mixing region 94, gradients of the cDNA in the material are reduced or eliminated. The mixing region 94 outputs the material including the cDNA to four pre-PCR zones 252a, 252b, 252c, 252d. Four blisters 86e, 86f, 86g, 86h are arranged respectively above the four pre-PCR zones 252a, 252b, 252c, 252d. The four pre-PCR zones 252a. 252b, 252c, 252d output material respectively to the four PCR zones 254a, 254b, 254c, 254d. Additionally, the four blisters 86e, 86f, 86g, 86h can output primer including fluorescent markers to the material to be analyzed respectively in the four PCR zones 254a, 254b, 254c, 254d.

In an embodiment, DNA based cells (bacteria and other cells) can be analyzed. In this case, a DNA trapping region can be substituted for the RNA binding region. The trapped DNA can go directly to amplification in a PCR region 96.

Figure 14:
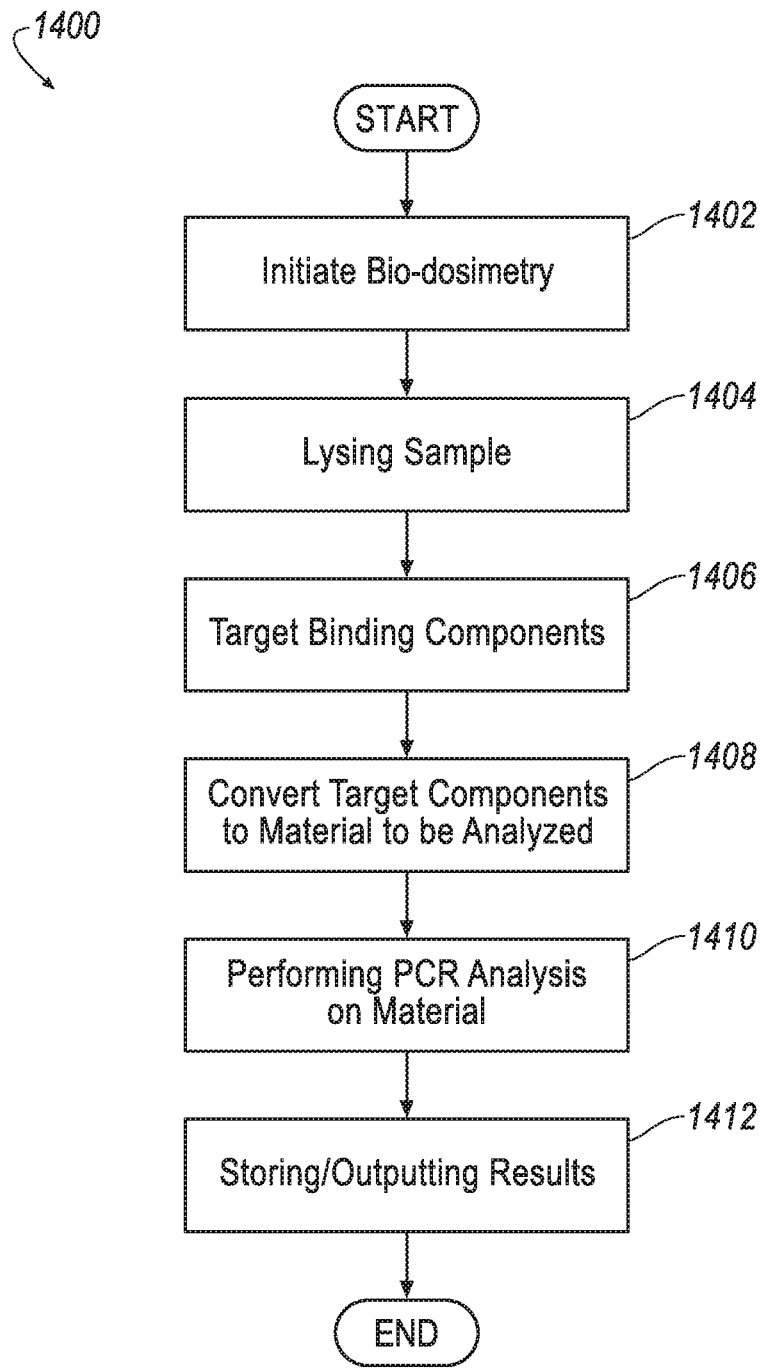
FIG. 14 is a diagram of an example process for performing bio-dosimetry.

FIG. 14 is a diagram of an exemplary process 1400 for performing bio-dosimetry on a sample with the bio-dosimetry system 10. A sample size can be in a range of 1 to 1000 microliters and can typically be approximately 100 microliters. An example sample is a drop of blood. The process 1400 begins in a block 1402.

In the block 1402, the computer 50 is programmed to initiate bio-dosimetry on a sample. The computer 50 may receive a trigger event, such as an input from the user via the user input device 30 to begin the bio-dosimetry process 1400, or inputs, for example from sensors 56, that the sample is available in the reservoir 22 and a fresh cartridge 14 has been inserted into the bio-dosimetry device 12. Based on the trigger event, the computer 50 may instruct the micropump 82 on the cartridge 14 to pump the sample from the reservoir 22 into the lysing region 90 on the cartridge 14. Alternatively, in a case that the cartridge 14 does not include the micropump 82, the computer 50 may instruct a pump 64 on the bio-dosimetry device 12 to pump the sample into the lysing region 90. The process 1400 continues in a block 1404.

In the block 1404, the computer 50 is programmed to lyse the sample according to process 1500, described below. Lysing the sample is defined herein as breaking the sample into component parts. Upon lysing the sample, the process 1400 continues in a block 1406.

In the block 1406, the computer 50 is programmed to bind target components of the sample in the binding region 92 according to a process 1600, described below. Target components are components of the sample that the bio-dosimetry system 10 targets to remove from the lysed sample and contain in the binding region 92. During the binding process, target components in the lysed sample are bound to the stationary phase 202 in the binding region 92, and other components are discarded. The process 1400 continues in a block 1408.

In the block 1408, the computer 50 is programmed to convert target components from the sample bound in the binding region 92 to a material to be analyzed by PCR according to the process 1700, described below. For example, mRNA, bound in the binding region, can be converted to cDNA. Upon converting the bound target components into material to be analyzed by PCR, the process 1400 continues in a block 1410.

In the block 1410, the computer 50 is programmed to perform PCR analysis on the material to be analyzed according to the process 1800 described below. The process 1400 continues in a block 1412.

In the block 1412, the computer 50 is programmed to store and/or output results of the PCR analysis. The computer 50 may output data on the display 28 on the bio-dosimetry device 12. Additionally or alternatively, the computer 50 may transmit the data, for example via wireless communications to another computer. Still further, the computer 50 may be programmed to store the data from the PCR analysis for retrieval at a future time. Upon outputting and/or storing the data, the process 900 may end.

Figure 15:
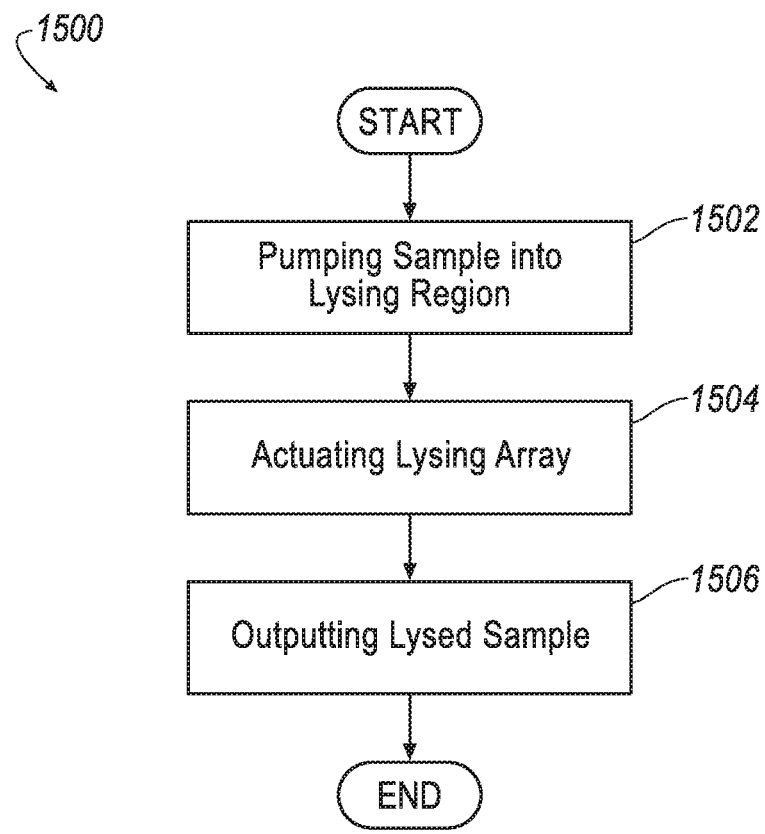
FIG. 15 is a diagram of an example process for lysing a sample.

FIG. 15 is a diagram of an exemplary process 1500 for lysing the sample received from the bio-dosimetry device 12 in an example lysing region 90. The sample to be lysed may be a drop of blood. Alternatively, the lysing region may be used to lyse other biological samples such as gram positive bacteria, gram negative bacteria, and encapsulated bacteria such as Anthrax. The process 1500 can be initiated by block 1404 of process 1400 and begins in the block 1502.

Figure 4:
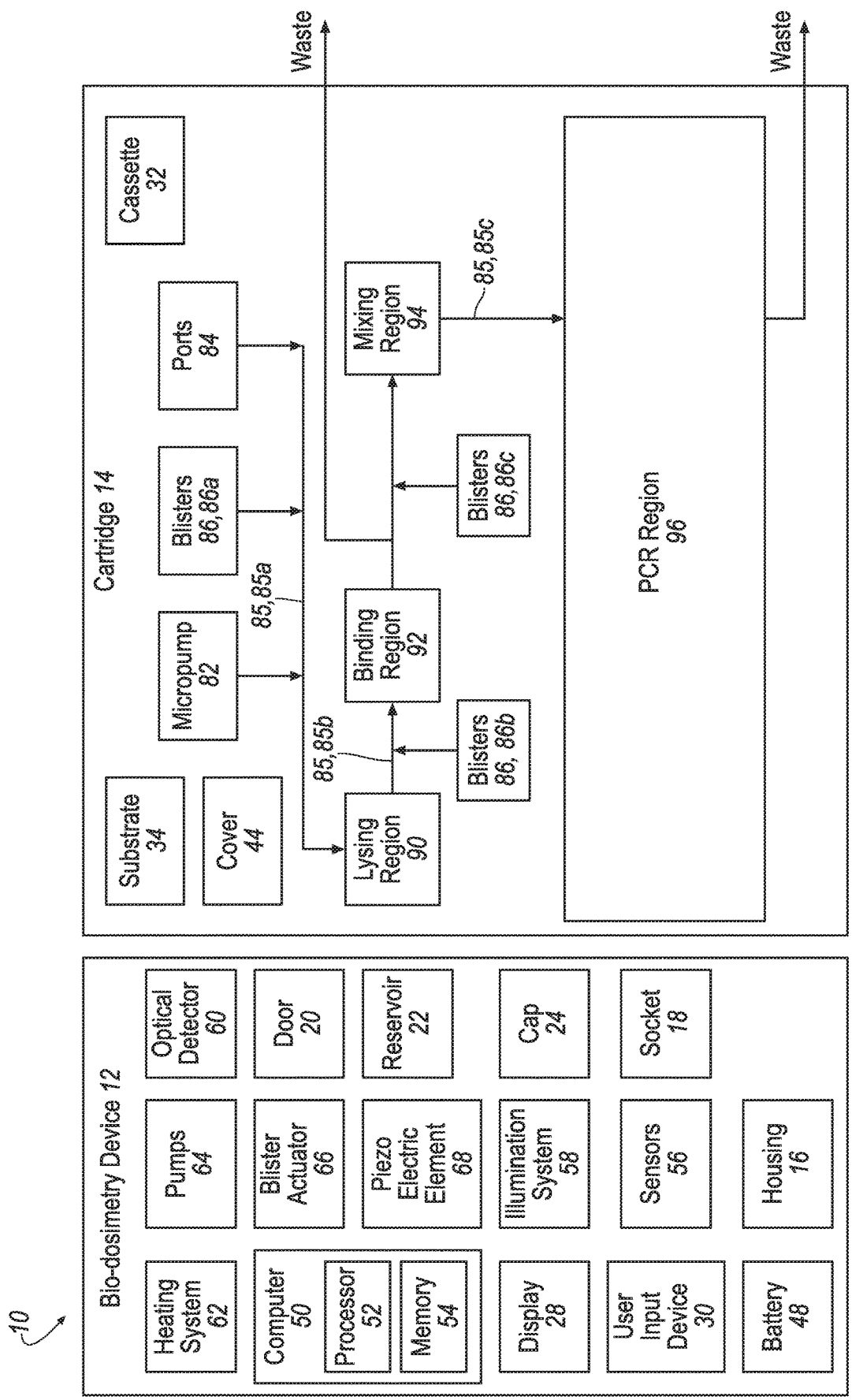
FIG. 4 is a block diagram of an example bio-dosimetry system including the bio-dosimetry device shown in FIGS. 1 and 2 and the cartridge shown in FIGS. 2 and 3.

In the block 1502, the computer 50 is programmed to pump the sample through the lysing region 90. For example, the sample may be a drop of blood or other liquid with a size of 100 microliters. A micropump 82 on the cartridge 14 may perform the pumping (FIG. 4). Alternatively, a pump 64 in the bio-dosimetry device 12 can perform the pumping. As an example, the sample can be pumped at a flow rate corresponding to a resonance time within the cavity 160 of the lysing array 134 in a range of 5 to 30 seconds. With an average resonance time of 20 seconds, and a cavity volume of four microliters, a sample can be lysed within a time of five minutes or less. The process 1500 continues in a block 1504.

In the block 1504, which can occur concurrently with all or a portion the block 1502, the computer 50 is programmed to apply ultrasonic stimulation to the lysing array 134. The lysing array 134 may include a piezo electric layer 166 as shown in FIG. 6C. Alternatively, the lysing array 134 may be coupled to a piezo electric element 68, included in the bio-dosimetry device 12, as shown in FIG. 6D. The computer 50 is programmed to activate the piezo electric layer 166 or piezo electric element 68 to induce flexing of the diaphragm 155 in the lysing array 134. At points of maximum flexing, for example near a center of the diaphragm 155, a displacement of the diaphragm 155 may be in a range from one to 100 microns, with a typical displacement of 5 microns, and may be in a direction substantially perpendicular to a plane of the diaphragm 155. The induced movement can typically be at a frequency of 20 kHz, with a range between 10 kHz and 40 kHz. The range is not intended to be limiting, and other frequencies above or below this range can also be used.

Based on the induced flexing of the diaphragm 155, the micropillars 162 will be induced to move laterally, back and forth through their respective non-stimulated positions in the lysing array 134. The induced lateral motion of the micropillars 162 can transfer mechanical energy to the sample, causing the sample to break into component parts. In an example, the sample includes human blood. Blood cells (leukocytes and/or erythrocytes) can be broken up to free mRNA from the cells. The process 1500 continues in a block 1506.

In the block 1506, that can occur concurrently with all or a portion of the blocks 1502 and 1504, the computer 50 is programmed to output the lysed sample to the binding region 92. Based on pressure from one of the micropump 82 and the pump 64, as described with regard to block 1502, the lysed sample passes through the outlet manifold 136, through a microchannel formed in the substrate, and into the binding region 92. The process 1500 ends.

Figure 16:
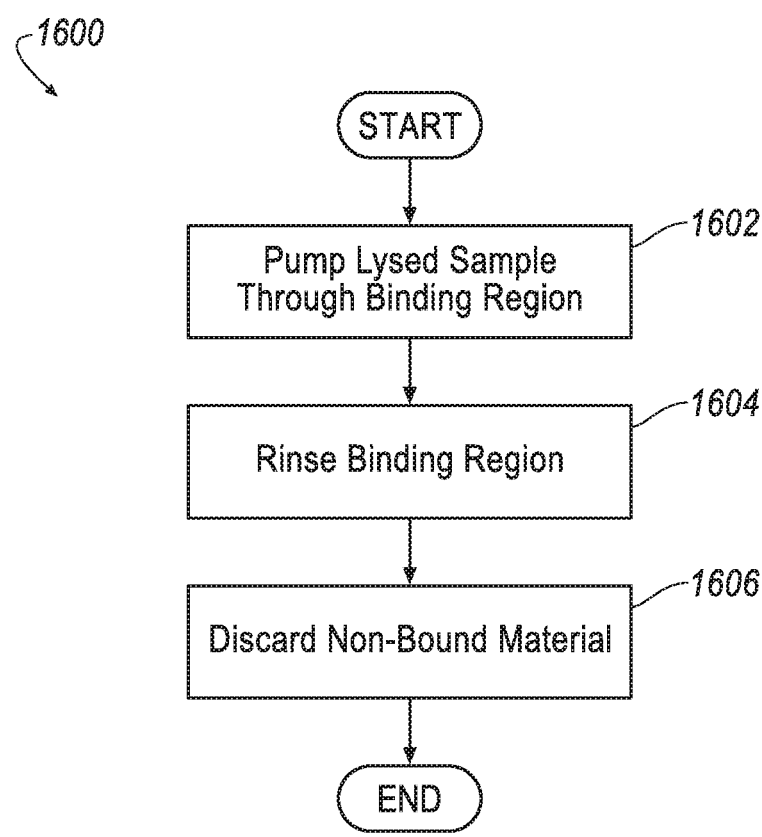
FIG. 16 is a diagram of an example process for binding components of the sample.

FIG. 16 is a diagram of an exemplary process 1600 for binding components of the sample in the binding region 92. The process 1600 can be initiated by block 1406 of process 1400 and begins in a block 1602.

In the block 1602, the computer 50 is programmed to pump the lysed sample through the binding region 92. The block 1602 can occur concurrently with all or a portion of the process 1500, as described above. That is, one of the micropump 82 or the pump 64 can pump the sample into the lysing region 90 and continue pumping such that the sample continues to flow into the binding region 92. As described above, a volume of the sample in a typical case can be 100 microliters. The volume of the lysing array 134 can be in a range of four microliters. Accordingly, a portion of the sample can have exited the lysing region 90 and entered the binding region 92 while another portion of the sample has not yet entered the lysing region 90, such that a continuous flow exists from the reservoir 22, through the lysing region 90 and through the binding region 92.

As the lysed sample flows through the binding region 92, the binding region 92 binds to target components in the sample, containing the target components. As described above, the binding region 92 includes a stationary phase 202. The stationary phase 202 includes a plurality of micropillars 220. The micropillars 220 may be coated with a binding material that binds with target components in the lysed sample.

As the lysed sample flows through the binding region 92, the target components bind with the binding material coated on the micropillars 220. During the block 1602, a sufficient quantity of the lysed sample can be passed through the binding region 92 such that the binding material on the stationary phase 202 is saturated. That is, substantially every site available to bind with a target component is occupied by a target component. As an example, the target components may be mRNA cells. The binding material may be oligo dT25 that specifically binds to any mRNA present in the sample. An amount of lysed sample through the binding region 92 to saturate the stationary phase 202 for a set of target components can be determined empirically. For example, for the binding region 92 as described above, including a stationary phase 202 coated with oligo dT25, a quantity of lysed sample of 60 microliters was determined to be sufficient to saturate the stationary phase 202.

As the sample continues to be pumped through the lysing region 90 and the binding region 92, waste material, after passing through the binding region, can be discarded. The computer 50 can be further programmed to turn off the micropump 82 or pump 64 when sufficient material has been passed through the binding region to saturate the stationary phase 202. The process 1600 continues in a block 1604.

In the block 1604, the computer 50 is programmed to rinse the binding region 92. The computer 50 sends instructions to force a rinsing fluid through the binding region 92. For example, the rinsing fluid may be contained in a blister 86 arranged at the inlet 203 of the binding region 92. The computer 50 may instruct a blister actuator 66 in the bio-dosimetry device 12 to actuate the blister 86. The blister actuator 66 may extend a plunger into the blister 86, expelling contents of the blister 86 into the binding region 92. The rinsing fluid may be selected to be a material that mixes with the non-bound material in the binding region but does not react with the target components. In this manner, the target components can remain bound in the binding region 92 after rinsing. The process 1600 continues in a block 1606.

In the block 1606, which can occur during all or a portion of the block 1604, the non-bound material, mixed with the rinsing fluid is discarded. The process 1600 ends.

Figure 17:
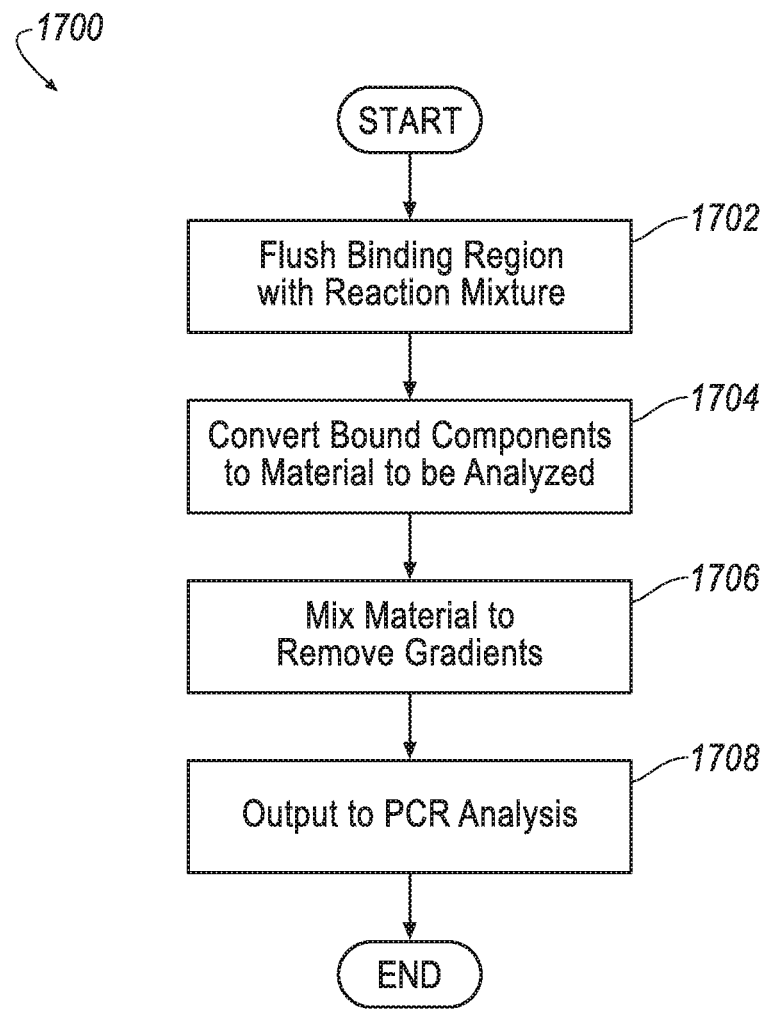
FIG. 17 is a diagram of an example process for converting components of the sample to material for analysis.

FIG. 17 is a diagram of an exemplary process 1700 for converting the target components of the sample, bound in the binding region 92, to material for analysis. The process 1700 can be initiated by block 1408 of process 1400 and begins in a block 1702.

In the block 1702, the computer 50 is programmed to flush the binding region 92 with a reaction mixture. For example, the cartridge 14 can include a blister 86b containing the reaction mixture fluidly coupled to the inlet 203 of the binding region 92. The computer 50 can instruct a blister actuator 66 to actuate the blister 86b such the reaction mixture is forced into and through the binding region 92. The reaction mixture can include the components necessary to convert the bond target components in the binding region 92 to material to be analyzed.

In an example, the target components may be mRNA from the sample. The reaction mixture can include the components necessary to convert, through reverse transcription, the mRNA to cDNA which can then be subjected to PCR analysis. The process 1700 continues in a block 1704.

In the block 1704, components in the reaction mixture react with the target components that are bound in the binding region 92, forming material to be analyzed. In some cases, heat may be applied to the binding region 92 to cause/support the reaction. For example, in the case of forming cDNA from mRNA bound in the binding region 92, the computer 50 cay be programmed to heat the binding region 92 to 50° C. for 30 minutes. The newly formed material may be bound to the stationary phase 202 of the binding region 92. The process 1700 continues in a block 1706.

In the block 1706, the computer 50 is programmed to release the material to be analyzed for analysis. For example, in the case that the material to be analyzed is cDNA, the cDNA may be bound to the stationary phase 202. In this case, the computer 50 can be programmed to heat the binding region to 84° C. for 5 minutes+sufficient time to release the cDNA. A time that is sufficient to release the cDNA can be determined empirically by performing tests with sample cartridges 14. The process 1700 continues in a block 1708.

In the block 1708, the computer 50 is programmed to remove gradients of the material to be analyzed in the reaction mixture. The computer 50 sends commands to pump the reaction mixture through the mixing region 94. As the reaction mixture flows through the mixing region 94, the material to be analyzed, for example, cDNA, is distributed throughout the reaction mixture, reducing or eliminating gradients of the cDNA. The process 1700 ends.

Figure 18:
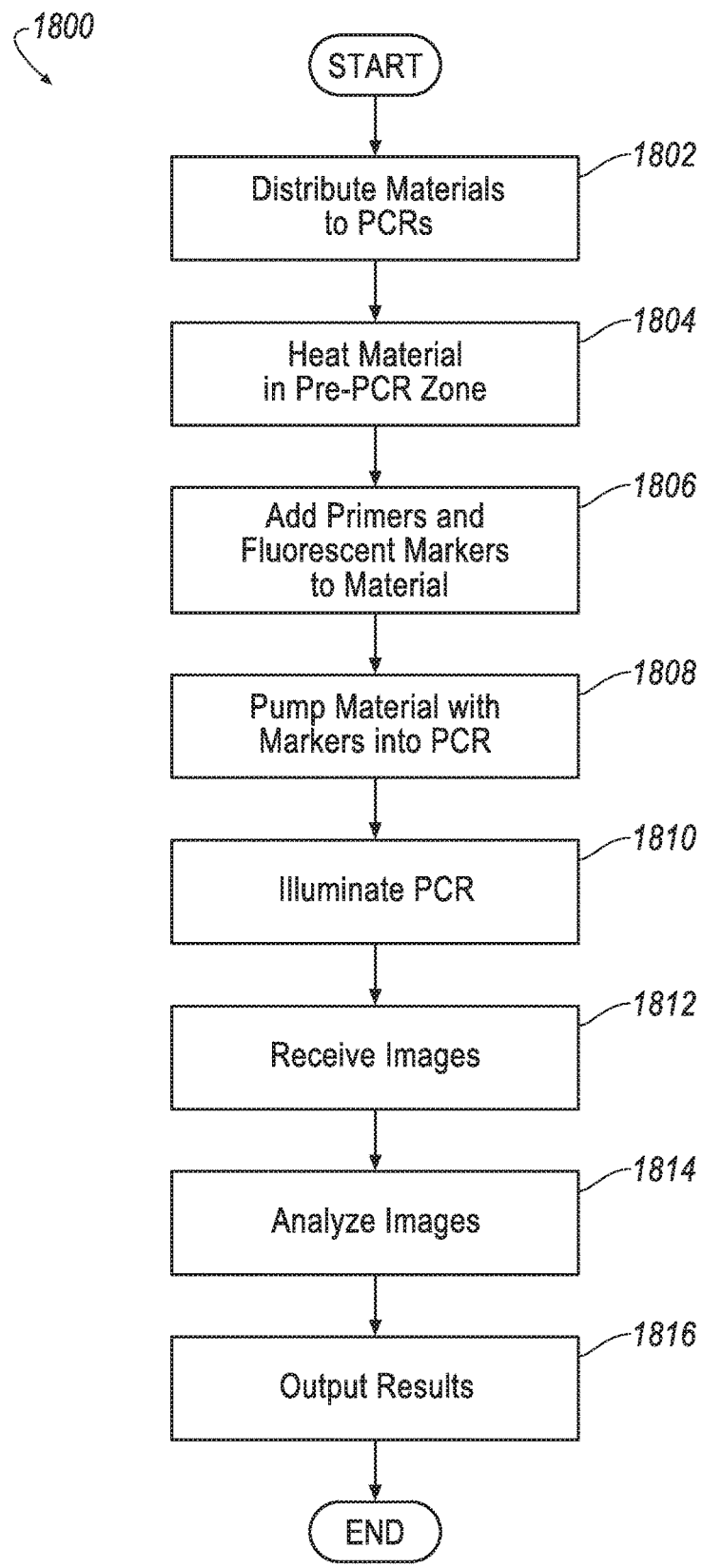
FIG. 18 is a diagram of an example process for performing PCR on the material for analysis.

FIG. 18 is a diagram for a process 1800 for performing qPCR analysis on the material to be analyzed. The process 1800 includes thermally cycling the material to be analyzed between a first temperature and a second temperature, and then imaging the material to be analyzed using fluorescent markers. The process 1800 can be initiated by block 1410 of process 1400 and begins in a block 1802.

In the block 1802, the computer 50 is programmed to distribute the reaction mixture including the material to be analyzed to four PCR channels 250a, 250b, 250c, 250d for analysis. The four PCR channels 250a, 250b, 250c, 250d include respectively four pre-PCR zones, 252a, 252b, 252c, 252d. As shown in FIG. 9, the four pre-PCR zones 252a, 252b, 252c, 252d (collectively pre-PCR zones 252) may be associated respectively with the four PCR zones 254a, 254b, 254c, 254d. The computer 50 can activate a pump 64 to pump the reaction mixture into the pre-PCR zones 252a, 252b, 252c, 252d.

In an example, the microchannel 85 coupling the mixing region 94 to the four pre-PCR zones 252a. 252b, 252c, 252e can split into four sub-channels 98a, 98b, 98c, 98d. The reaction mixture including the material to be analyzed can be pumped through the microchannel, and divide between the four sub-channels 98a, 98b, 98c, 98d, under pressure from the pump 64, such that a portion of the reaction mixture including the material to be analyzed is directed toward each of the four pre-PCR zones 252a, 252b, 252c, 252d.

The process 1800 continues in a block 1804.

In the block 1804, the computer 50 may be programmed to heat the reaction mixture including the material to be analyzed in the pre-PCR zones 252a, 252b, 252c, 252d. For example, the material to be analyzed may include cDNA. The computer 50 may be programmed to heat the reaction mixture including the material to be analyzed, to separate the cDNA into single strands prior to adding the primers and markers. The computer 50 may be programmed to heat the reaction mixture to 95° C. for 10 minutes. Other temperatures and times can be used for different materials to be analyzed. The times and temperatures can be determined empirically. The process continues in a block 1806.

In the block 1806, the computer 50 is programmed to add a set of markers and primers to the reaction mixture flowing respectively into each of the four PCR zones 254a, 254b, 254c, 254d. A different set of markers may be used respectively for each of the four PCR zones 254a, 254b, 254c, 254d. For example, as shown in FIG. 9, a first blister 86e may be coupled to add markers and primers to a microchannel between the pre-PCR zone 252a and PCR zone 254a, a second blister 86f may be coupled to add markers and primers to a microchannel between the pre-PCR zone 252b and PCR zone 254b, a third blister 86g may be coupled to add markers and primers to a microchannel between the pre-PCR zone 252c and the PCR zone 254c and a fourth blister 86h may be coupled to add markers and primers to a microchannel between the pre-PCR zone 252d and the PCR zone 254d. At a time that the reaction mixture including the material to be analyzed is flowing from the pre-PCR zone 252a to PCR zone 254a, the computer 50 may actuate the first blister 86e. At a time that the reaction mixture including the material to be analyzed is flowing from the pre-PCR zone 252b to PCR zone 254b, the computer 50 may actuate a second blister 86f. Similarly, the computer 50 may actuate a third blister 86g at a time that the reaction mixture including the material to be analyzed is flowing from the pre-PCR zone 252c to PCR zone 254c and a fourth blister 86h at a time that the reaction mixture including the material to be analyzed is flowing from the pre-PCR zone 252d to PCR zone 254d. The times that the reaction mixture is flowing respectively from pre-PCR zone 252a to PCR zone 254a, from pre-PCR zone 252b to PCR zone 254b, from pre-PCR zone 252c to PCR zone 254c and from pre-PCR zone 252d to PCR zone 254d may be the same, partially overlapping, or different, depending on an organization of the microchannel and four sub-channels between the mixing region 94 and the four pre-PCR zones 252. For example, each of the four sub-channels coupling the respective pre-PCR zones 252a, 252b, 252c, 252d to the microchannel coming from the mixing region 94, may be a same length or a different length. The lengths of the sub-channels may impact a timing for adding the sets of markers to the reaction mixture for the respective PCR zones 254a, 254b, 254c, 254d.

The primers for each PCR zone 254 are selected to mark prepare a particular component or pair of components in the material to be analyzed for qPCR analysis. For example, for each of the four PCR zones 254a, 254b, 254c, 254d, respective primers containing fluorescent markers may be selected to allow two genes (or DNA sequences) to be evaluated simultaneously. One gene may be an endogenous control (EC) gene that is stable with regard to exposure to radiation. An example EC gene is RB1. A second gene may be a radiation response gene. Examples of radiation response genes include CDKN1A, ASTN2, and GDF15. The process continues in a block 1808.

In the block 1808, the computer 50 is programmed to pump the reaction mixture, including the material to be analyzed and combined with the primers, into the respective PCR zones 254a, 254b, 254c, 254d. The blocks 1808 through 1816 will be described with respect to an example PCR zone 254. It can be understood that the process of block 1808 can be applied similarly to each of the PCR zones 254a, 254b, 254c, 254d.

The computer 50 may, for example, instruct a pump 64 in the bio-dosimetry device 12 to pump the reaction mixture including the material to be analyzed and the primers into the example PCR zone 254. As described above, the PCR zone 254 includes a microchannel 300. The microchannel 300 is formed of a plurality of segments. Each segment extends back and forth between a first heating region 310, a detection region 320 and a second heating region 330. In an example, the microchannel 300 includes 35 segments.

As an example, the material to be analyzed includes cDNA. The computer 50 may be programmed to maintain a first temperature of the first heating region at 95° C. and to maintain second temperature of the second heating region at 60° C. As the reaction mixture together with the material to be analyzed and the primer passes through the first heating region 310, the 95° C. temperature causes the cDNA to separate into single strands. As the reaction mixture together with the material to be analyzed and the primer passes through the second heating region 330, the 60° C. temperature allows single stranded primers to attach to single stranded DNA to form complementary strands. As the reaction mixture continues to pass through the segments of the microchannel 300, the material to be analyzed continues to thermally cycle, that is, to cycle between the first and second heating regions 310, 330 at a rate of one cycle per segment, such that, with each consecutive segment, a greater number of strands of the cDNA form complementary strands with the primer.

The computer 50 can be programmed to continue to pump the reaction mixture in the PCR zone 254 until all or most of the microchannel 300 is filled with the reaction mixture. In this case, the farther through the microchannel 300 the reaction mixture has passed, the greater number of cycles of the first and second heating regions the reaction mixture will have experienced. The process 1800 continues in a block 1810.

In the block 1810, the computer 50 is programmed to illuminate the microchannel 300 in the PCR zone 254. The computer 50 may radiate the detection region 320 of the PCR zone 254 with light for a time. The time may be in a range of from 1 to 2000 seconds, with a typical time of 1200 seconds. The process 1800 continues in a block 1812.

In the block 1812, the computer 50 receives images from the detection region 320 of the PCR zone 254. The fluorescent markers that combined with the cDNA will fluoresce at wavelengths determined by the markers. The optical detector 60 in the bio-dosimetry device 12 receives the light fluoresced from the markers. Before being received by the optical detector 60, a filter may be used to select which wavelength of light can be received by the optical detector 60. As described above, in the case that different markers were used for two different components of the material to be analyzed (e.g., two different genes), a first image can be received from the detection region 320 with a first filter for a first range of wavelengths and a second image can be received from the detection region 320 with a second filter for a second range of wavelengths. The optical detector 60 can provide data representing the first and second images to the computer 50. The process 1800 continues in a block 1814.

In the block 1814, the computer 50 analyzes the data of the first and second images. For example, the computer 50 may determine the Ct of each of the genes combined with a respective fluorescent marker. The Ct (cycle threshold) is defined as the number of cycles required for the fluorescent signal to exceed background level. The number of cycles required for the fluorescent signal to exceed the background level can be determined by a position within the PCR detection region 320 along an axis of increasing cycles that shows a radiation of light at the wavelength of the particular fluorescent material that exceeds the radiation of the background. The position can be directly correlated to a number of cycles to which the material to be analyzed (i.e., the genes with the fluorescent material currently being measured) were exposed before their collective illumination exceeded the background illumination. A measurement taken with an example PCR zone is described below in reference to FIGS. 22A, 22B, 22C. The process 1800 continues in a block 1816.

In the block 1816, the computer 50 reports and/or stores the results of the PCR analysis. The computer 50 may report the results to another computer and/or on a display such as the display 28 on the bio-dosimetry device 12. Further, the computer 50 may store the results, for example with a time stamp, or an identification of the cartridge that was measured, in memory associated with the computer 50. The process 1800 ends.

As used herein, the adverb "substantially" modifying an adjective means that a shape, structure, measurement, value, calculation, etc. may deviate from an exact described geometry, distance, measurement, value, calculation, etc., because of imperfections in materials, machining, manufacturing, data collector measurements, computations, processing time, communications time, etc.

As an example, the bio-dosimetry system 10 can be used to determine radiation exposure of an individual. A drop of blood from the individual can be evaluated to determine the radiation dose they received based on their gene expression levels. As evidence of efficacy ex vivo irradiation of human blood was utilized and the subsequent culturing of that blood for quantitative study of utilizing gene expression for human dosimetry.

Figure 19A:
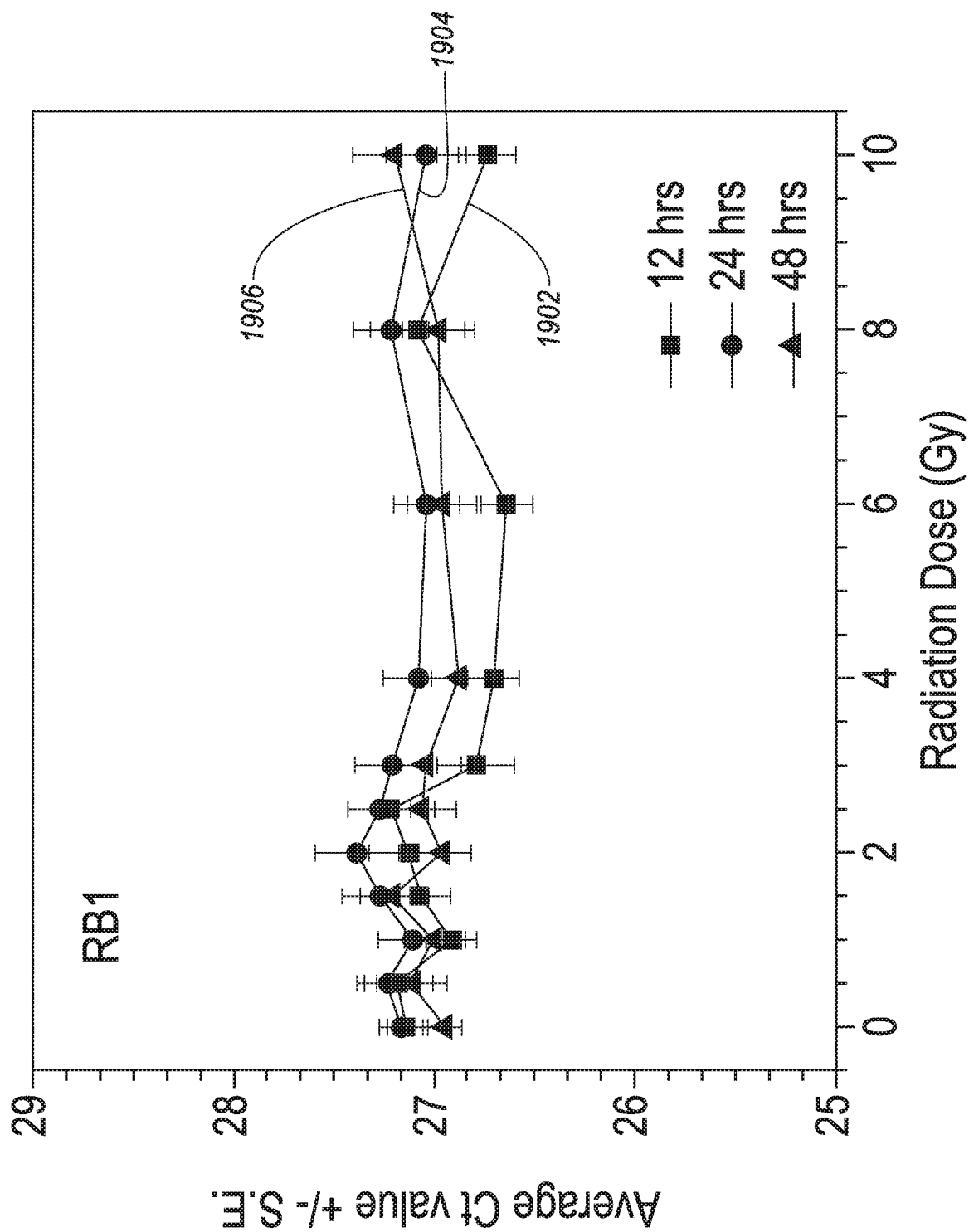
FIGS. 19A-19E are graphs illustrating example responses of a respective genes to radiation.

Selection of valid control genes is critical to have a point of reference to evaluate radiation responsive genes. Several very stable endogenous control (EC) gene products were identified. As an example, FIG. 19A illustrates a fold increase in expression level as a function of dose for the gene RB1 at 12 hours (trace 1902), 24 hours (trace 1904 and 48 hours (trace 1906). This EC gene is stable with respect to dose and time. It is also stable in its expression across all donors in our study.

Having selected a series of EC genes as controls, radiation responsive genes can be evaluated by examining the gene expression level of a potential response gene relative to that of a selected EC gene for exposed sample. A fold increase in expression levels as a function of dose and time following exposure can be determined by comparing that ratio to the population average of the non-exposed ratio of those same genes. The results for three potential radiation response genes (CDKN1A, ASTN2, and GDF15) that can be utilized as dosimetry biomarkers as shown respectively in FIGS. 19B, 19C and 19D referenced to RB 1.

Figure 19B:
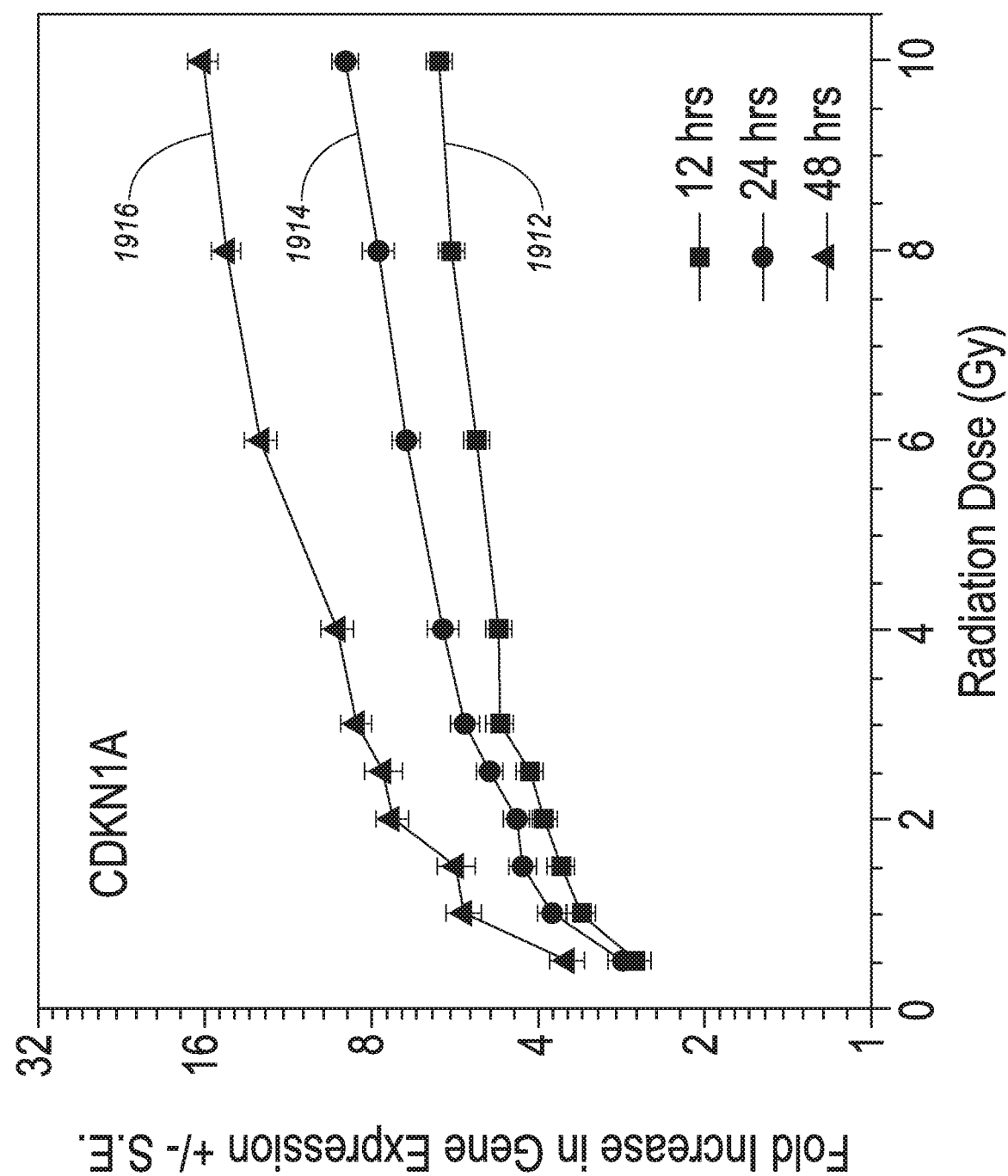

FIG. 19B illustrates a fold increase of expression level as a function of dose for the gene CDKN1A at 12 hours (trace 1912), 24 hours (trace 1914) and 48 hours (trace 1916).

Figure 19C:
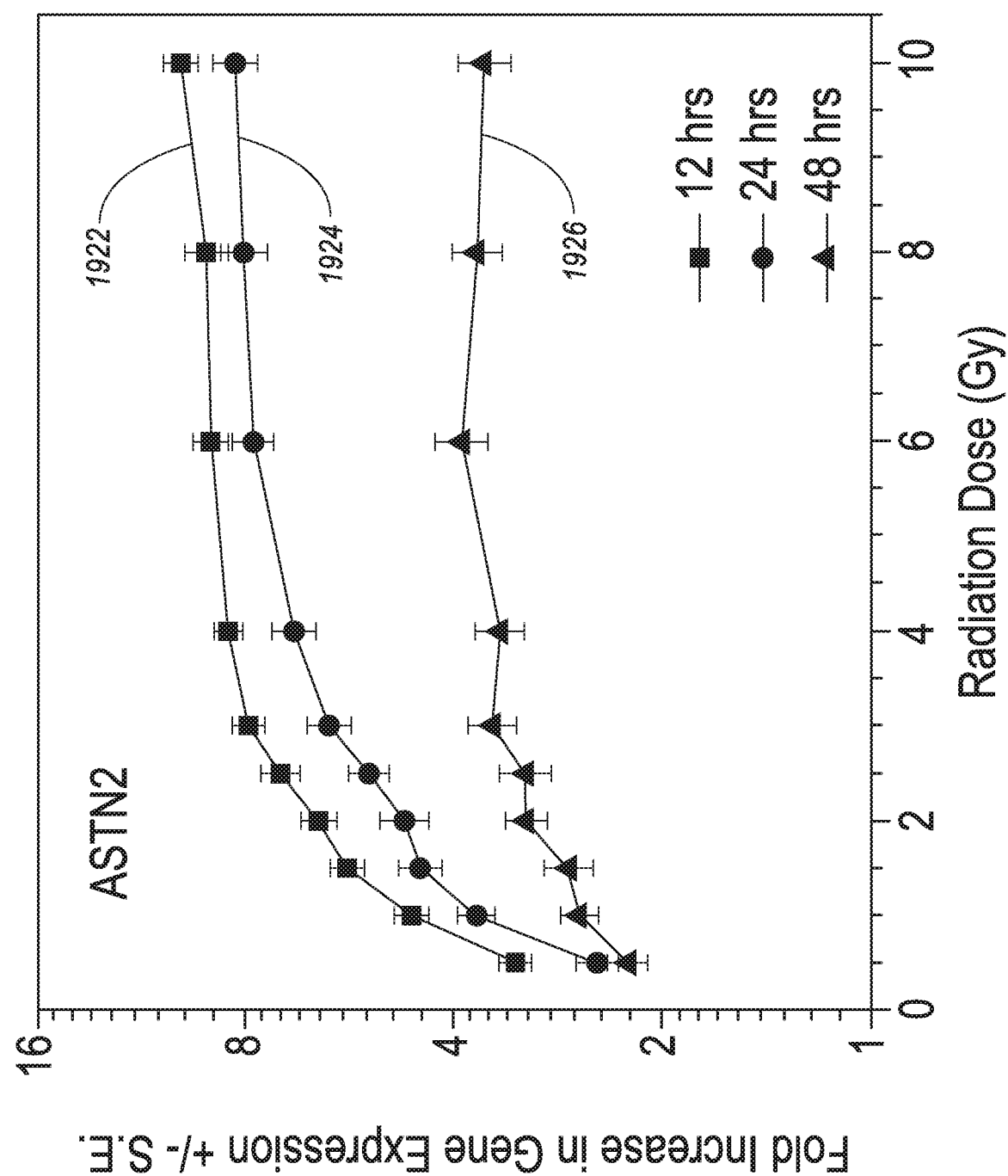

FIG. 19C illustrates a fold increase of expression level for the gene ASTN2 at 12 hours (trace 1922) 24 hours (trace 1924) and 48 hours (trace 1926).

Figure 19D:
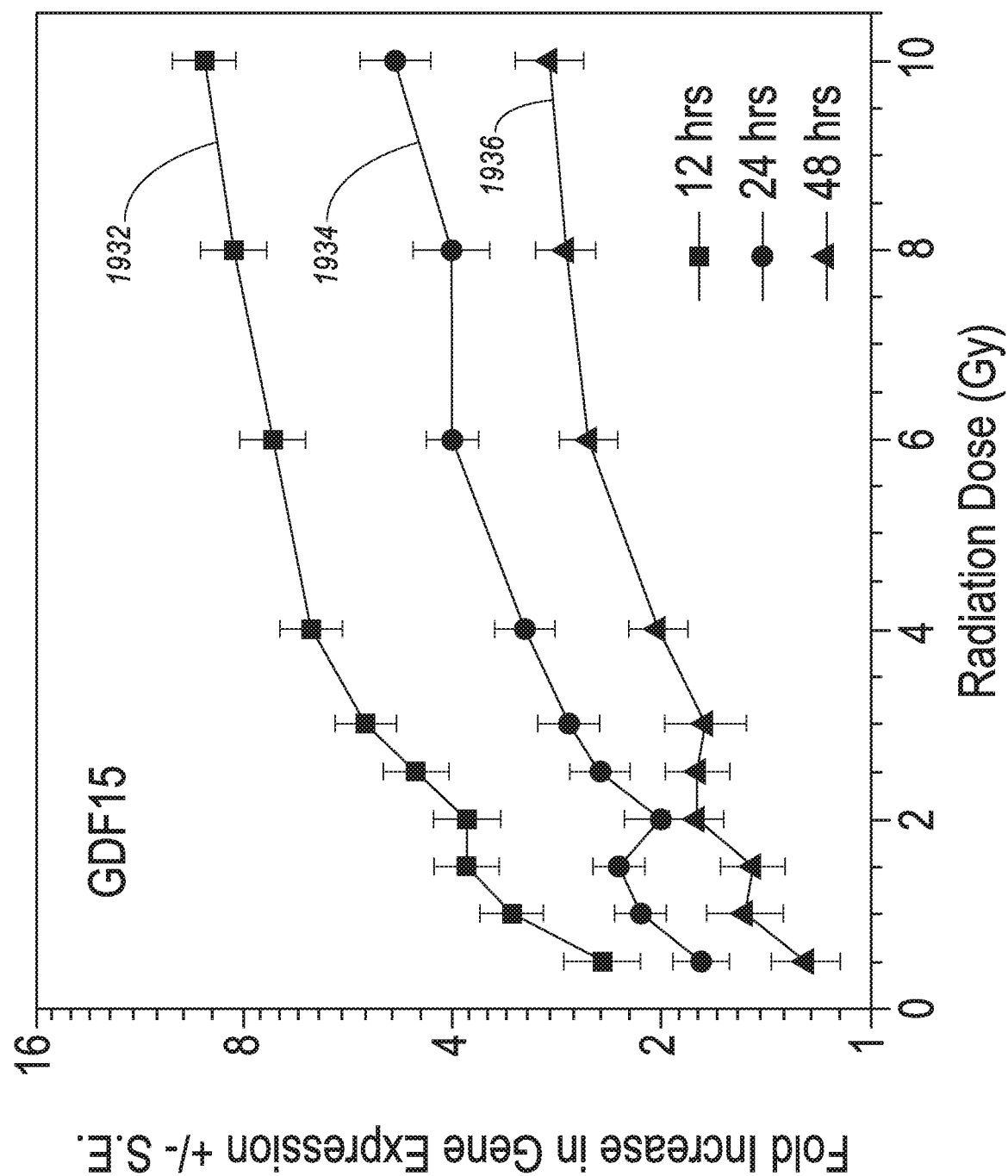

FIG. 19D illustrates a fold increase of expression level as a function of dose for the gene GDF15 at 12 hours (trace 1932), 24 hours (trace 1934) and 48 hours (trace 1936).

For each of these genes CDKN1A, ASTN2 and GDF15, the curves show clear increases in expression for each of the times post irradiation examined. In a case of a nuclear event, the time of the nuclear event is known. A user can, in this case, follow the appropriate dosimetry curve for each gene product. All the gene products shown, and many others, exhibit significant increases in genes expression even at doses as low as 0.5 Gy. In the case of some genes, up to 16-fold increases of expression can be observed at higher doses. Fold changes in gene expression of 1.5 or 2 are large can easily and accurately be detected by qPCR analysis, indicating that these changes will be readily detectable by a portable PCR system.

In the case of several radiation responsive genes such as CDKN1A (FIG. 19B) gene expression levels slowly increase with time post-exposure and were highest at the longest time point examined in our studies. While other gene products such as ASTN2 and GDF15 (FIGS. 19C and 19D) rapidly increase at very short times post exposure and then decrease with time, they still maintain an easily-detectable increase in expression out to 48 hours post exposure. Also of note is that while a number of gene products such as CDKN1A and GDF15 (FIGS. 19B and 14D) show a response to radiation over the entire range of doses examined, other gene products such as ASTN2 (FIG. 19C) show a relatively steep dose response over a short range of doses and plateau in their expression at higher doses. This wide range in dose and time responses observed in the radiation response genes identified provides the ability to select a series of genes that can be utilized and optimized for dosimetry at various exposure levels and times post exposure.

Figure 19E:
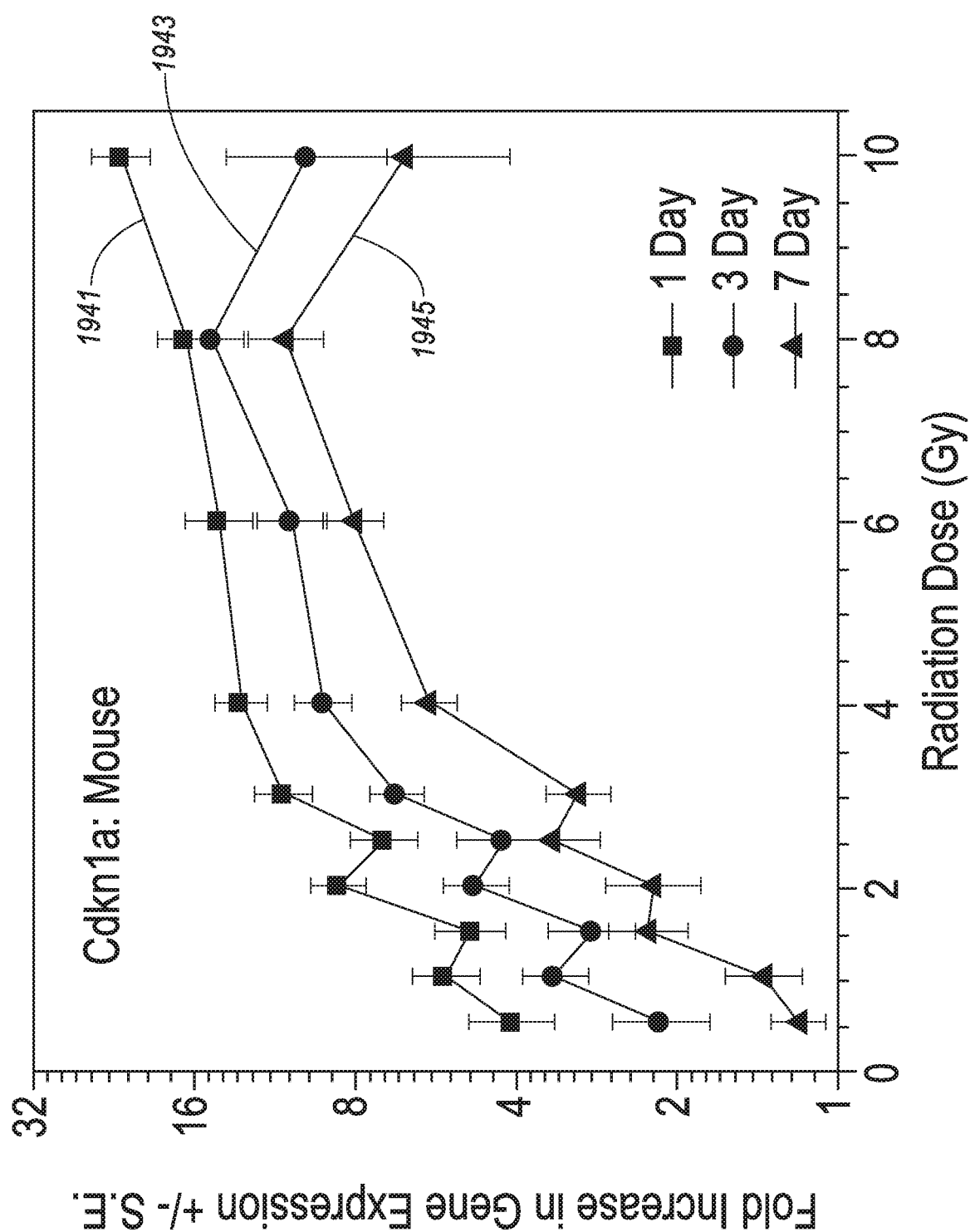

FIG. 19E illustrates a fold increase of expression of the gene CDKN1A v. dose for a in vivo radiation utilizing an animal model (C57Bl/6 male mice). Traces 1941, 1943 and 1945 show the fold increase in expression of CDKN1A v. dose respectively at 1 day, 3 days and 7 days. Although direct comparisons of gene expression levels between humans and mice cannot be made, the measurements indicate that fold increases in CDKN1A expression due to radiation exposure in vivo can be detected in the animal models.

Figure 19F:
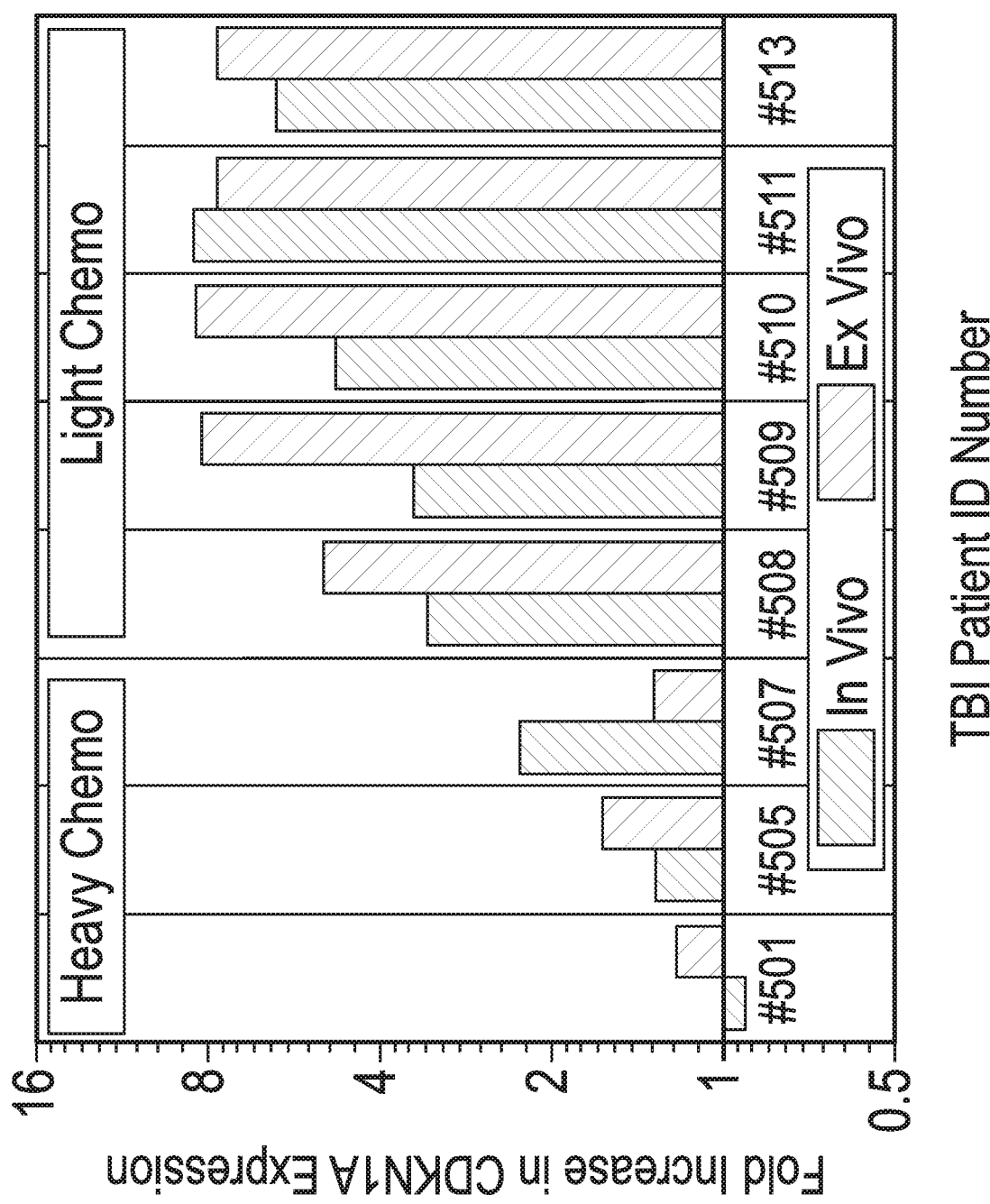
FIG. 19F is a graph comparing example in vivo and ex vivo gene responses to radiation.

FIG. 19F illustrates a comparison between human cancer patients irradiated in vivo and blood samples from these patients irradiated ex vivo. Sample of blood was drawn from the patients immediately prior to the patient receiving total body irradiation doses of between 2 and 4 Gy from a Cobalt 60 source A portion of the pre-radiation therapy blood sample was then irradiated with the same source and conditions as that received by the patient, and this blood was then cultured in the absence of mitogen for 24 hours. A second blood sample was drawn from the patient at approximately 24 hours post exposure. An in vivo/ex vivo exposure comparison for one of the genes examined (CDKN1A) was referenced to DPM1. Similar increase in gene expression can be observed in both the in vivo and ex vivo irradiated samples for each patient. In this study (#501, #505, #507) were given higher levels of chemotherapy while the later patients (#509, #510, #511, #513) were given lower doses of chemotherapy in their treatment. In these later patients (#509, #510, #511, #513), increases in gene expression from in vivo exposure closely match those seen in ex vivo exposure for CDKN1A shown as well as for other genes examined, and in several cases such as CDKN1A expression increases match those seen in samples from healthy donors. The fact that gene expression levels for several genes, which could be utilized for radiation dosimetry, remain viable as biomarkers even in cancer patients receiving light doses of chemotherapy is a good indication of the robustness of these markers and to their potential resistance to confounding factors in the general population.

Both the results from our mouse study and our evaluation of TBI patients support the validity of the use of ex vivo irradiated blood as a valid model for radiation exposure in humans for the study of gene expression from a blood sample. The animal study showed that comparable gene expression increases, resulting from radiation exposure, occur in an in vivo irradiation animal model as those seen with the ex vivo irradiation of cultured blood samples. The animal study further confirms that gene expression is a valid and feasible dosimetry method even at times of seven days post exposure and possible beyond. In vivo/ex vivo comparisons of gene expression levels in human cancer patients confirm that increases in gene expression due to radiation exposure for the genes examined in our study are not dependent on whether the radiation exposure was performed in vivo or ex vivo.

Figure 20A:
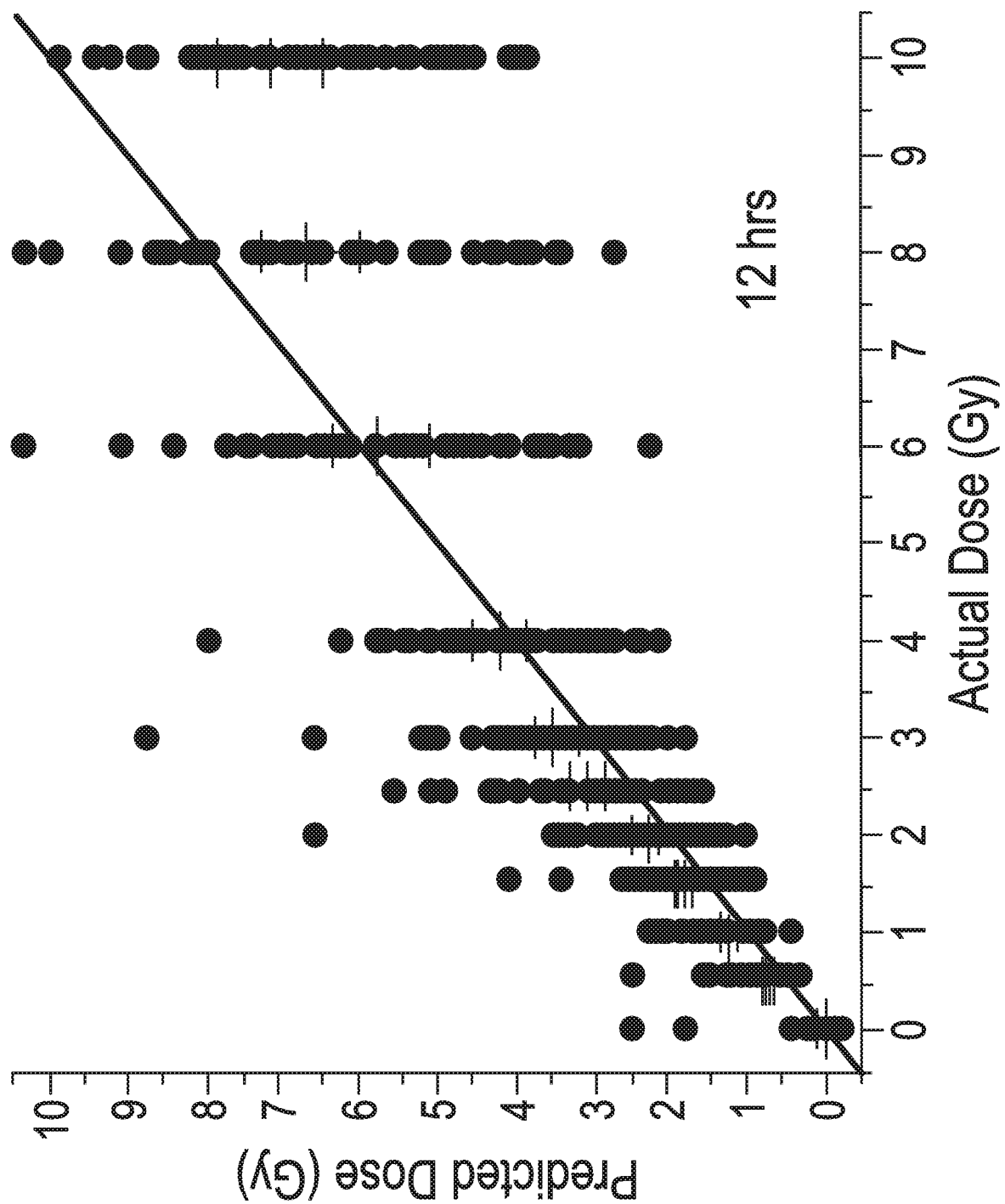
Figure 20B:
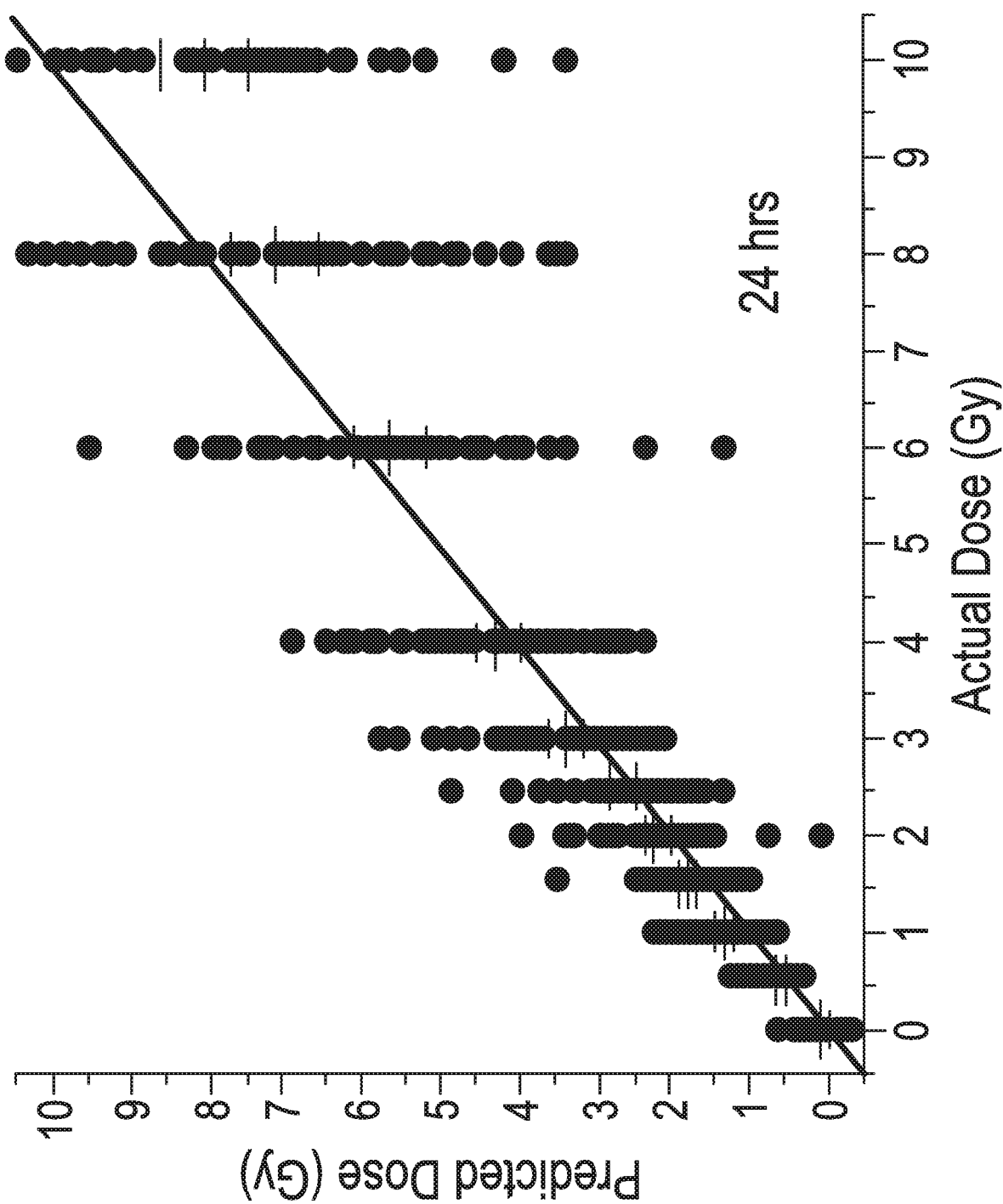

The results from individual genes as shown in FIGS. 19A-19F illustrate a time dose dependence to the genes expression levels. To accurately perform dosimetry based on data from these genes, a statistical model is required. To develop a statistical model, multiple predictive models to determine dosimetry were developed for the various time points post exposure. These regression models, a quadratic fit to the log of dose, were fit using forward stepwise regression. At each step a gene was added to the model based on the following: (a) the greatest contribution to increasing R-squared and (b) maintaining the available sample size. The statistical model for time point post exposure is shown in FIGS. 20A-20C where the actual radiation dose is plotted against the model's predicted dose. The genes utilized in this model were CDKN1A, ATM, ASTN2, and GDF15. FIG. 20A-20C compare modeling results with ex vivo human data respectively for 12 hours, 24 hours and 48 hours post exposure.

While the modeling of the gene expression data is modeled with respect to the log of dose, due to the exponential nature of Ct values, this data is converted to a linear scale for the plots in FIGS. 20A-20C. It is this conversion from the native log scale of the model to a linear dose for plotting that makes the data at high doses in FIGS. 20A-20C appears to be more scattered then at the lower doses.

Figure 20D:
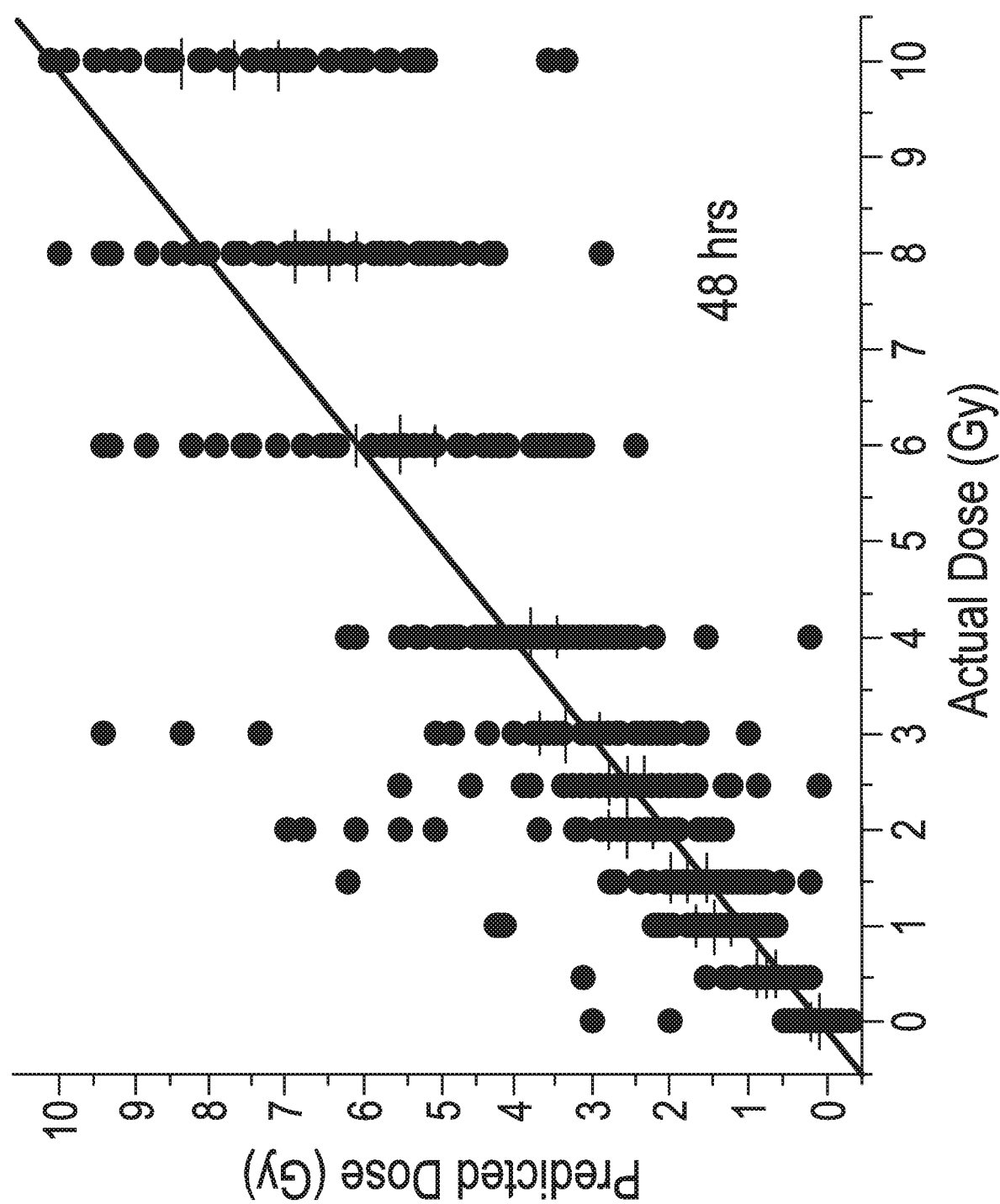
FIG. 20D illustrates an example receiver operating characteristic (ROC) for modeling exposure to radiation at 12 hours post exposure.

An example result is shown in FIG. 20D where a receiver operating characteristic (ROC) curve for a prediction of exposure of 2 Gy or greater is shown at 12 hours post exposure. For the data shown in FIG. 20D, the area under the ROC curve was 0.9816 (value of 1 being perfect), which is very good for biomedical screening application. Similar ROC curves were obtained for the predictive models for the other post exposure time points examined in the ex vivo human study and for the data from the animal model. In order to further reduce any false negatives, sensitivity could be maximized at the cost specificity resulting in increased false positives.

Figure 21:
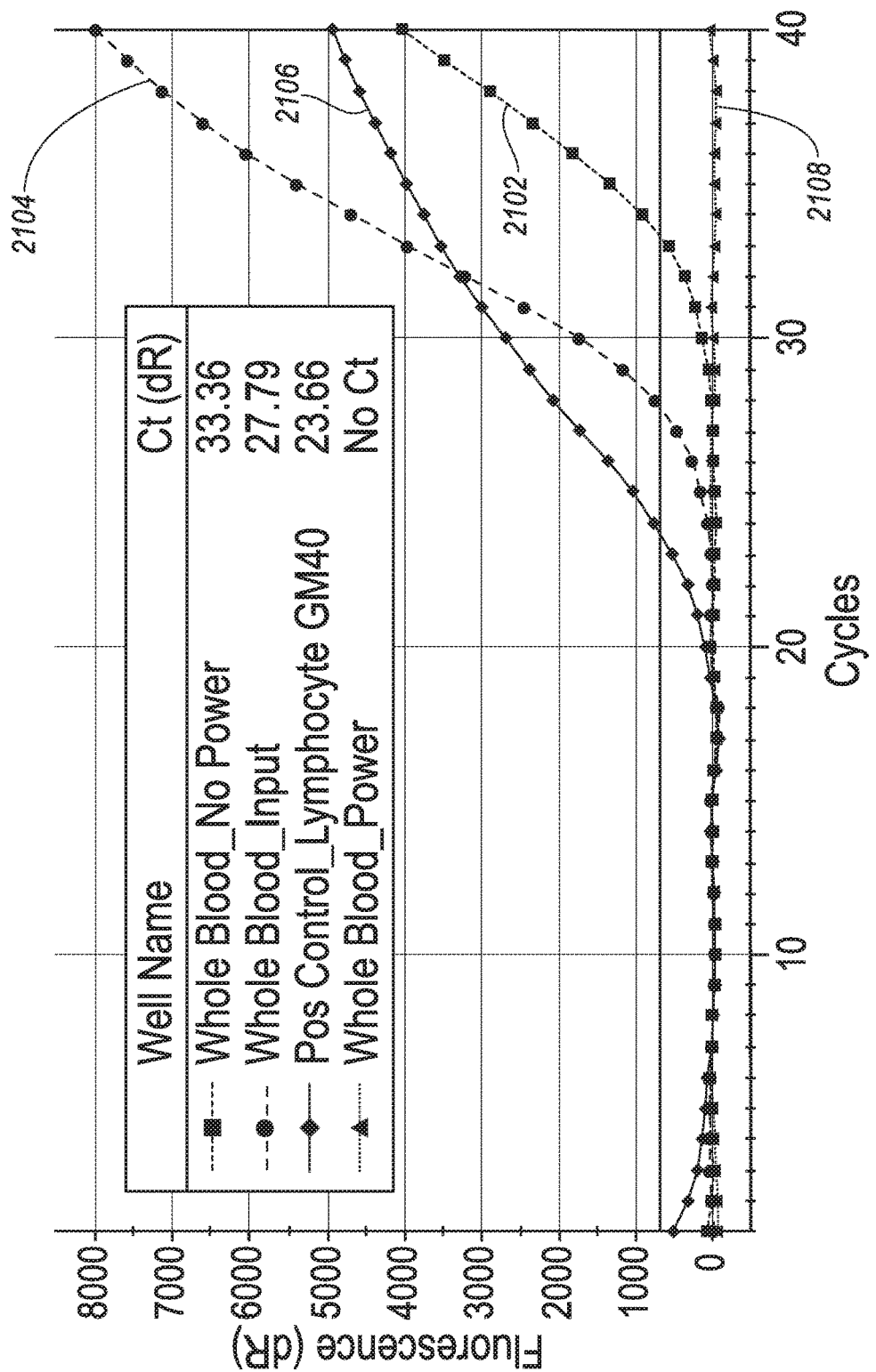
FIG. 21 illustrates example graphs of fluorescence v. cycles from PCR analysis of blood samples with varying degrees of lysing.

Tests were performed on an example lysing device to estimate the lysing capability of the lysing region 90 described above. The example lysing device used for the test had included 1600 micropillars arranged in a 40 by 40 lysing array. The micropillars were supported on a 6 mm×6 mm×0.1 mm thick diaphragm. The micropillars had a diameter of 0.075 mm and a height of 0.75 mm. The spacing between the micropillars was 0.075 mm. To estimate the effectiveness of the lysing region, PCR analysis was performed on four different samples exposed to varying degrees of lysing. The results are of the tests are shown in FIG. 21, which illustrates example traces of cycle threshold (Ct) from PCR analysis of the four different blood samples. The Ct level indicates a number of remaining unlysed lymphocites in each blood sample.

Trace 2102 in FIG. 21 is an example trace from PCR analysis of whole blood that is passed through an example lysing device without powering the lysing device.

Trace 2104 is an example trace from PCR analysis of whole blood that was not passed through the lysing device (a sample representing the condition of the blood as input into the lysing device).

Trace 2106 is an example trace from PCR analysis of a control_lynmphocyte GM40. The control lymphocyte is a set amount that is injected as a known control for reference.

Trace 2108 is an example trace from PCR analysis of whole blood that is passed through the lysing device under power. That is, the diaphragm is actuated at 20 kHz while the whole blood is passed through the lysing device.

Figure 22A:
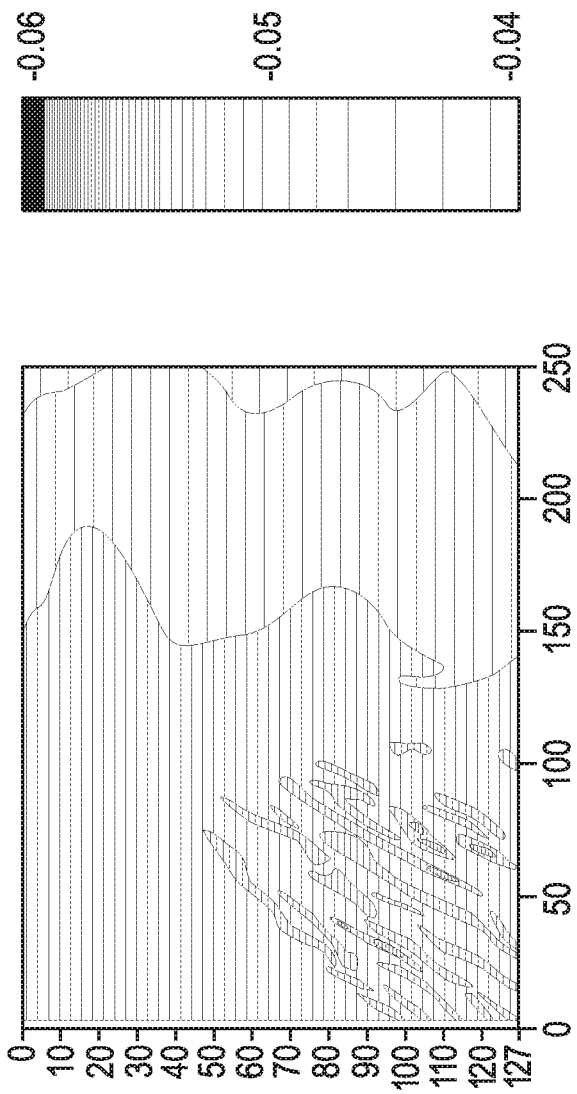
FIGS. 22A, 22B, 22C illustrate an example fluorescent image from a PCR zone.
Figure 22B:
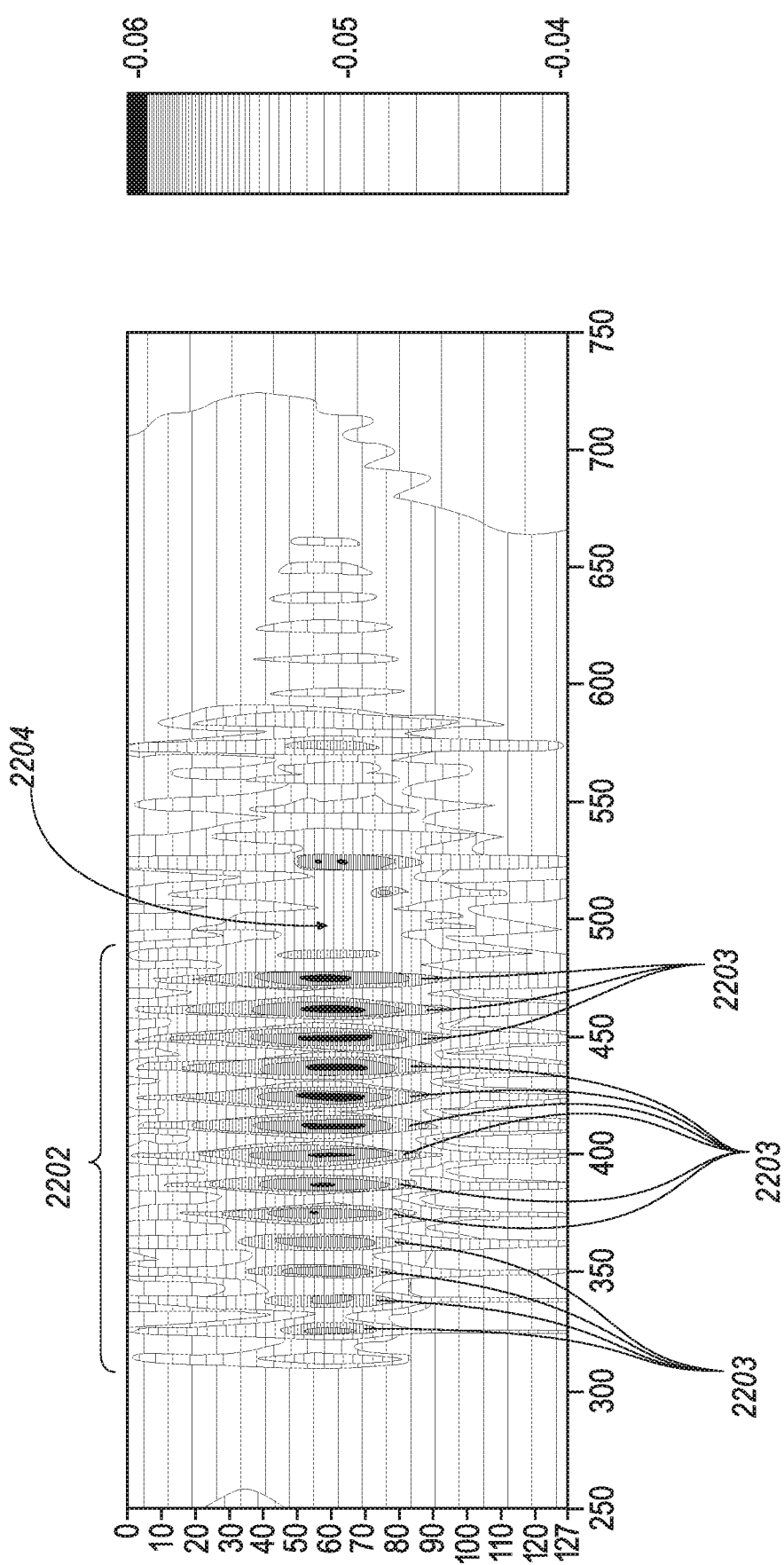
Figure 22C:
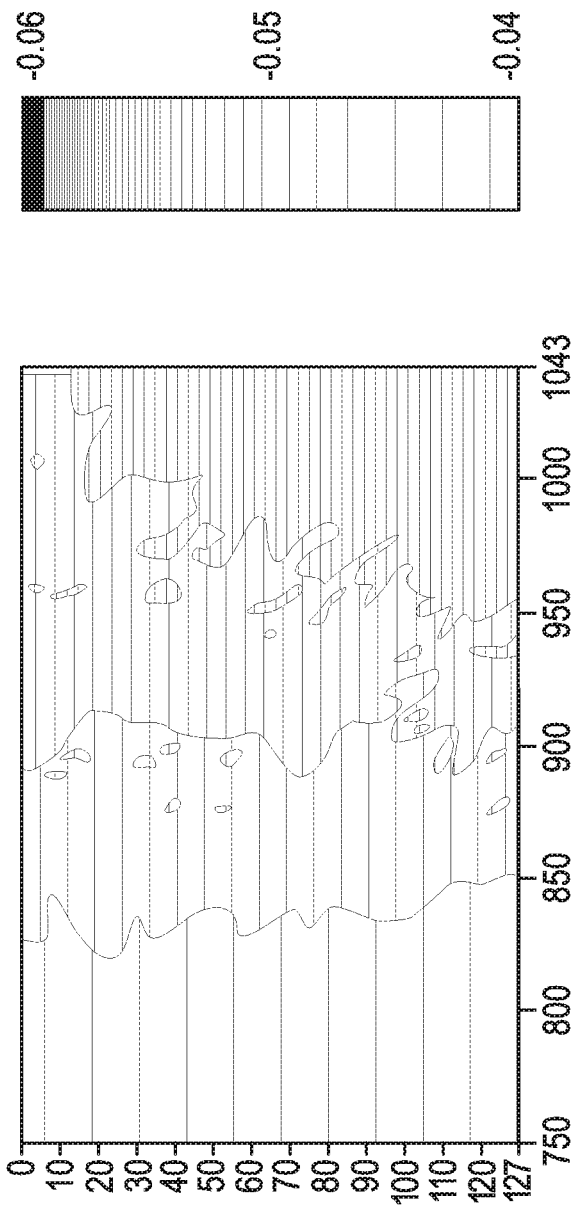

FIGS. 22A, 22B, 22C illustrates an example image of a PCR zone 254 containing material to be analyzed that has been illuminated and is fluorescing. As described above, the PCR zone 254 includes a microchannel 300 including a plurality of segments. Each segment cycles through a first heating region 310, a detection region 320 and a second heating region 330.

In the test, material to be analyzed is pumped into the microchannel 300 in the PCR zone 254. In an example, sufficient material can be pumped into the microchannel 300 that all of the plurality of segments contain material. When, the microchannel 300 is filled in this manner, the detection region 320 in the PCR zone 254 can be illuminated. Following illumination, an image can be taken of the detection region 320. The resulting image can show, by an intensity of fluorescent light at locations (i.e., in different segments) of the microchannel 300, the cycle threshold (Ct) required to detect a component (for example, a gene) within the material to be analyzed. The cycle threshold (Ct) is defined as the number of cycles (through the first and second heating regions 310, 330) required for the fluorescent signal from the tag to exceed background level. The cycle threshold provides an indication of a degree of exposure to radiation of the original sample used to prepare the material to be analyzed.

In FIGS. 22A, 22B, 22C, the number of cycles of the PCR to which the material to be analyzed has been exposed increases from left to right. FIG. 22A is a beginning (left) portion of the PCR zone 254. FIG. 22B is a middle portion of the PCR zone 254. FIG. 22C is an end (right) portion of the PCR zone 254. Imaging is performed in the detection region 320 between the first and second heating regions 310, 330 (see, for example, FIGS. 12A and 12C). In the area labelled 2202, the fluorescing signal from the material to be analyzed begins to exceed the background level. This is indicated by the dark oval shaped areas 2203 in the middle of the image. As can be seen, the intensity of the fluorescing signal continues to increase from left to right. This increasing discontinues at approximately a point 2204. This indicates that the material to be analyzed was only pumped into the PCR zone up to this point.

Figure 23:
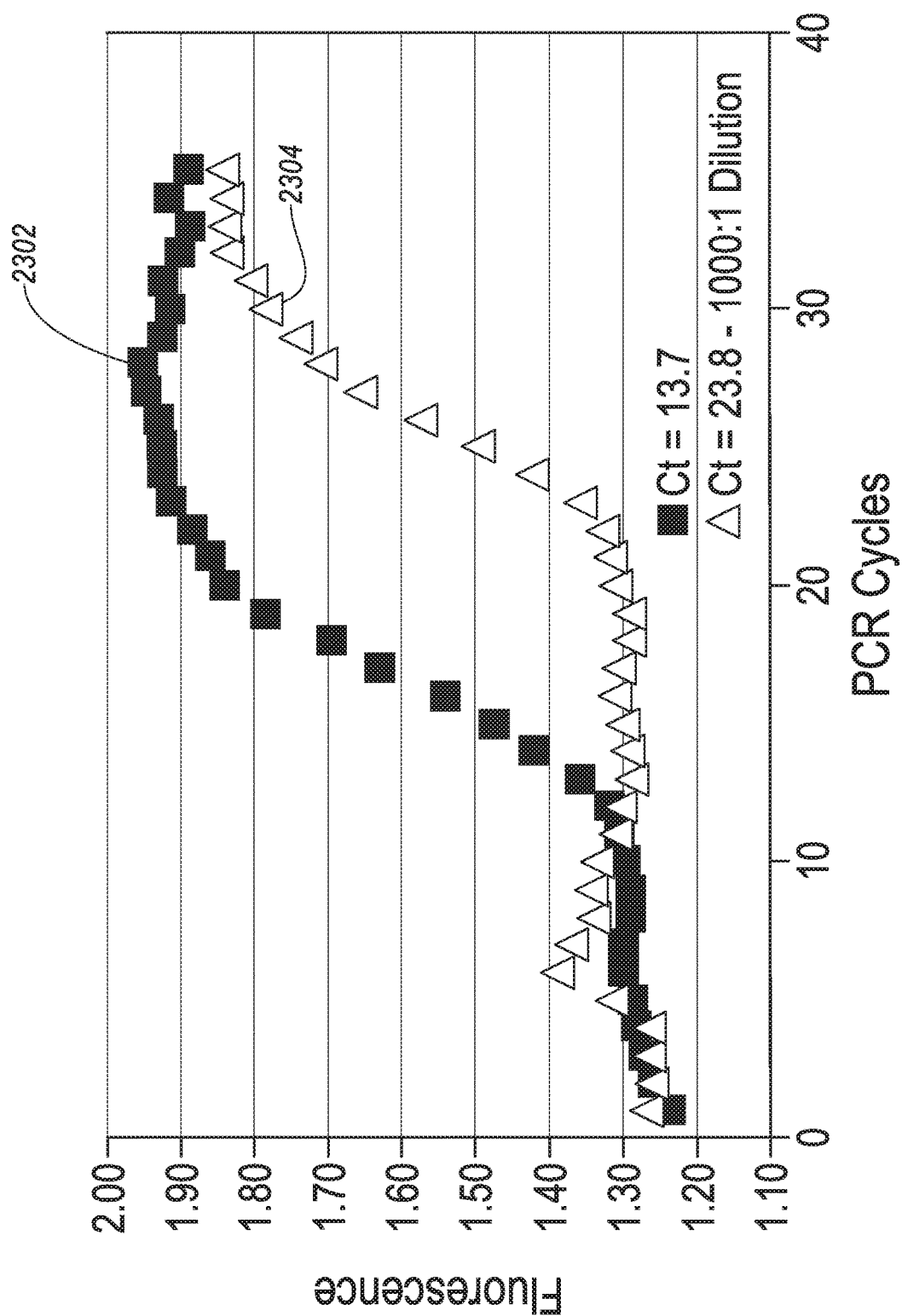
FIG. 23 illustrates an example amplification of two targeted genes with a PCR zone.

FIG. 23 shows an example amplification of two targeted genes with a PCR. The first target gene was cDNA made from human 18S rRNA. The sample was run through the sample PCR and yielded a Ct (PCR cycled threshold) value of 13.7 (trace 2302). The same sample was then diluted by a factor of 1 to 1000 and run on the PCR. This dilution should correspond to a Ct shift of ~10 cycles. The resulting trace 2304 corresponds well with this expected shift.

With regard to the media, processes, systems, methods, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of systems and/or processes herein are provided for the purpose of illustrating certain embodiments and should in no way be construed so as to limit the disclosed subject matter.

Accordingly, it is to be understood that the present disclosure, including the above description and the accompanying figures and below claims, is intended to be illustrative and not restrictive. Many embodiments and applications other than the examples provided would be apparent to those of skill in the art upon reading the above description. The scope of the invention should be determined, not with reference to the above description, but should instead be determined with reference to claims appended hereto and/or included in a non-provisional patent application based hereon, along with the full scope of equivalents to which such claims are entitled. It is anticipated and intended that future developments will occur in the arts discussed herein, and that the disclosed systems and methods will be incorporated into such future embodiments. In sum, it should be understood that the disclosed subject matter is capable of modification and variation.

The article "a" modifying a noun should be understood as meaning one or more unless stated otherwise, or context requires otherwise. The phrase "based on" encompasses being partly or entirely based on.

The invention claimed is:

1. A cartridge comprising a substrate including a lysing region including:
a cavity defined by the substrate and having a bottom and sides, the bottom of the cavity formed by a diaphragm, the diaphragm having a first side and a second side, wherein the diaphragm is formed in the substrate and has a first thickness that is reduced relative to a second thickness of the substrate in which it is formed;
a cover extending over a top of the cavity and coupled to the sides of the cavity;
a plurality of micropillars extending from the first side of the diaphragm into the cavity and having respective ends, such that applying an oscillating force on the second side of the diaphragm causes lateral motion of the ends of one or more of the micropillars, wherein the lateral motion is motion back and forth through an unstimulated position of a respectively micropillar of the one or more micropillars; and
a piezo electro layer coupled to the second side of the diaphragm, wherein the oscillating force is applied by the piezo electric layer.

2. The cartridge of claim 1, wherein the substrate is made of glass, silicon or a polymer.

3. The cartridge of claim 1, wherein the oscillating force is applied by a piezo electric element coupled to the second side of the diaphragm.

4. The cartridge of claim 1, wherein the micropillars are cylindrical.

5. The cartridge of claim 4, wherein a ratio of a height of a micropillar included in the plurality of micropillars from the first side of the diaphragm to the respective end of the micropillar and a diameter of the micropillar is greater than five.

6. The cartridge of claim 1, wherein the micropillars are arranged in an array including three or more rows and three or more columns.

7. The cartridge of claim 1, wherein the lysing region includes an inlet fluidly coupled to a first cavity side and an outlet fluidly coupled to a second cavity side, such that a liquid sample can pass through the cavity.

8. The cartridge of claim 7, wherein the lysing region includes an input distributor manifold fluidly coupled on a first side of the input distributor manifold to the inlet and fluidly coupled on a second side of the distributor manifold to the first cavity side, wherein the input distributor manifold broadens from the first side of the input distributor manifold to the second side of the input distributor manifold.

9. The cartridge of claim 1, wherein a frequency of oscillation of the diaphragm is greater than 100 Hertz.

10. The cartridge of claim 6, wherein the oscillating force is applied by a single piezo electric element coupled to the second side of the diaphragm and extending from a first row to a last row of micropillars along a first dimension of the array parallel to the columns of the micropillars and from a first column to a last column of micropillars of the array along a second dimension parallel to the rows of the micropillars.

11. The cartridge of claim 6, wherein the oscillating force is applied by a single piezo electric layer coupled to the second side of the diaphragm and extending from a first row to a last row of micropillars along a first dimension of the array parallel to the columns of the micropillars and from a first column to a last column of micropillars along a second dimension of the array parallel to the rows of the micropillars.

* * * * *